(12) United States Patent
Tang et al.

(10) Patent No.: US 12,110,302 B2
(45) Date of Patent: Oct. 8, 2024

(54) METAL COMPLEX, INTERMEDIATE, AND PREPARATION METHOD AND APPLICATION THEREOF

(71) Applicant: SHANGHAI INSTITUTE OF ORGANIC CHEMISTRY, CHINESE ACADEMY OF SCIENCES, Shanghai (CN)

(72) Inventors: Wenjun Tang, Shanghai (CN); Siyao Xu, Shanghai (CN)

(73) Assignee: SHANGHAI INSTITUTE OF ORGANIC CHEMISTRY, CHINESE ACADEMY OF SCIENCES, Shanghai (CN)

( * ) Notice: Subject to any disclaimer, the term of this patent is extended or adjusted under 35 U.S.C. 154(b) by 310 days.

(21) Appl. No.: 17/284,549

(22) PCT Filed: Oct. 10, 2019

(86) PCT No.: PCT/CN2019/110401
§ 371 (c)(1),
(2) Date: Oct. 4, 2022

(87) PCT Pub. No.: WO2020/073962
PCT Pub. Date: Apr. 16, 2020

(65) Prior Publication Data
US 2023/0114794 A1    Apr. 13, 2023

(30) Foreign Application Priority Data
Oct. 10, 2018 (CN) .......................... 201811178107.X

(51) Int. Cl.
*C07F 15/00* (2006.01)
(52) U.S. Cl.
CPC ................... *C07F 15/0073* (2013.01)
(58) Field of Classification Search
CPC .............. C07F 15/0073; C07F 9/65515; B01J 31/2419; B01J 31/24
See application file for complete search history.

(56) References Cited

FOREIGN PATENT DOCUMENTS

| CN | 103087105 A | 5/2013 |
|---|---|---|
| CN | 104650145 A | 5/2015 |
| CN | 105859783 A | 8/2016 |
| CN | 107445999 A | 12/2017 |
| WO | 2011056737 A1 | 5/2011 |

OTHER PUBLICATIONS

D. Liu, et al. Eur. J. Org. Chem. 646-649 (2005) (Year: 2005).*
W. Tang, et al. 12 Organic Letters 176-179 (2010) (Year: 2010).*
International Search Report (with English translation) and Written Opinion issued in PCT/CN2019/110401, dated Jan. 10, 2020, 11 pages provided.
Kagan et al., "Asymmetric catalytic reduction with transition metal complexes. I. Catalytic system of rhodium(I) with (-)-2,3-0-isopropylidene-2,3-dihydroxy-1,4-bis(diphenylphosphino)butane, a new chiral diphosphine", Journal of the American Chemical Society, Sep. 6, 1972, 94, 18, pp. 6429-6433.
Zhang et al., "Highly Enantioselective Hydrogenation of Cyclic Enamides Catalyzed by a Rh-PennPhos Catalyst", . J. Org. Chem., vol. 64, No. 6, Published Feb. 27, 1999, pp. 1774-1775.
Tang et al., "An ortho-substituted BIPHEP ligand and its applications in Rh-catalyzed hydrogenation of cyclic enamides ", Organic Letters, 2002, vol. 4, No. 10, pp. 1695-1698.
Dupau et al., Enantioselective Hydrogenation of the Tetrasubstituted C=C Bond of Enamides Catalyzed by a Ruthenium Catalyst Generated in situ, Advanced Synthesis & Catalysis, first published Jun. 8, 2001, pp. 331-334.
Salomo et al., "Highly Enantioselective Iridium-Catalyzed Hydrogenation of Cyclic Enamides", Wiley Online Library, Angewandte International Edition Chemie, first published May 17, 2016, pp. 7988-7992.

* cited by examiner

*Primary Examiner* — Alexander R Pagano
*Assistant Examiner* — Frank S. Hou
(74) *Attorney, Agent, or Firm* — HSML P. C.

(57) ABSTRACT

Provided is a metal complex as represented by formula I. The metal complex may be used as a catalyst for asymmetric catalytic hydrogenation, is capable of efficiently catalyzing and synthesizing a series of chiral p-aryl amides having high optical purity, and is especially capable of asymmetrically catalyzing and hydrogenating a tetra-substituted enamide compound, chiral amides having high optical purity are synthesized, and the carrying amount of ligand may reach 100,000.

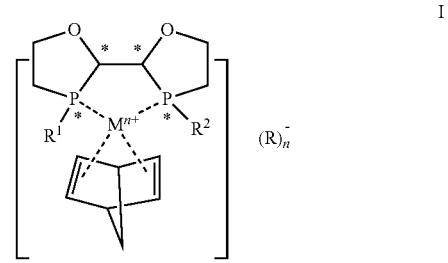

10 Claims, 1 Drawing Sheet

METAL COMPLEX, INTERMEDIATE, AND PREPARATION METHOD AND APPLICATION THEREOF

This application claims the priority of Chinese patent application 201811178107X filed on 2018 Oct. 10. The contents of the Chinese patent application mentioned above are incorporated herein by reference in its entirety.

FIELD OF THE INVENTION

The invention relates to a metal complex, intermediate, preparation method and application thereof.

BACKGROUND OF THE INVENTION

Since chiral phosphine ligands were firstly applied by Knowles to transition metal-catalyzed asymmetric hydrogenation in 1968, the field of asymmetric hydrogenation has made great progress. In 1972, Kagan reported the first asymmetric hydrogenation of paraenamides (H B Kagan, T P Dang, *J. Am. Chem. Soc.* 1972, 94, 6429.). After that, enamides was extensively studied as a kind of important hydrogenation substrates and a series of significant results were achieved.

The asymmetric hydrogenation of tetra-substituted β-aryl cycloalkenamide is a kind of widely investigated and successful asymmetric hydrogenation of tetra-substituted cycloalkenamide. In 1999, Professor Zhang Xumu ((a) Z. Zhang, G. Zhu, Q. Jiang, D. Xiao, X. Zhang, *J. Org. Chem.* 1999, 64, 1774-1775; (b) W. Tang, Y. Chi, X. Zhang, *Org. Lett.* 2002, 4, 1695-1698.) achieved the asymmetric hydrogenation of tetra-substituted cycloalkenamides for the first time with the ee value of 73%~98% (yield 80~99%) in the asymmetric hydrogenation of cycloalkenamide using the catalytic system of Rh and Me-Pennphos, but having the much limited substrate range. Subsequently, Bruneau et al. (P. Dupau, C. Bruneau, P H Dixneuf, *Adv. Synth. Catal.* 2001, 343, 331-334.) also tried asymmetric hydrogenation of tetra-substituted cycloalkenamide substrates via the catalytic system of Ru and Me-DuPhos or Me-BPE ligand, but only moderate yield (60%-95%) and enantioselectivity (73%-98%) were obtained.

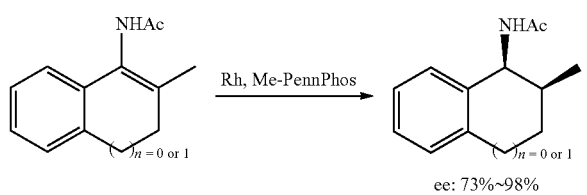

Recently, Riera reported (E. Salomo, S. Orgue, A. Riera, X. Verdaguer, *Angew. Chem. Int. Ed.* 2016, 55, 7988-7992.) asymmetric hydrogenation catalyzed by the Ir-MAXPHOX system, also achieving the catalytic effect similar to Rh or Ru (as shown in the figure below).

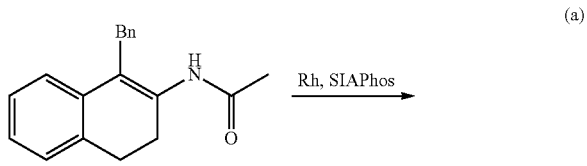

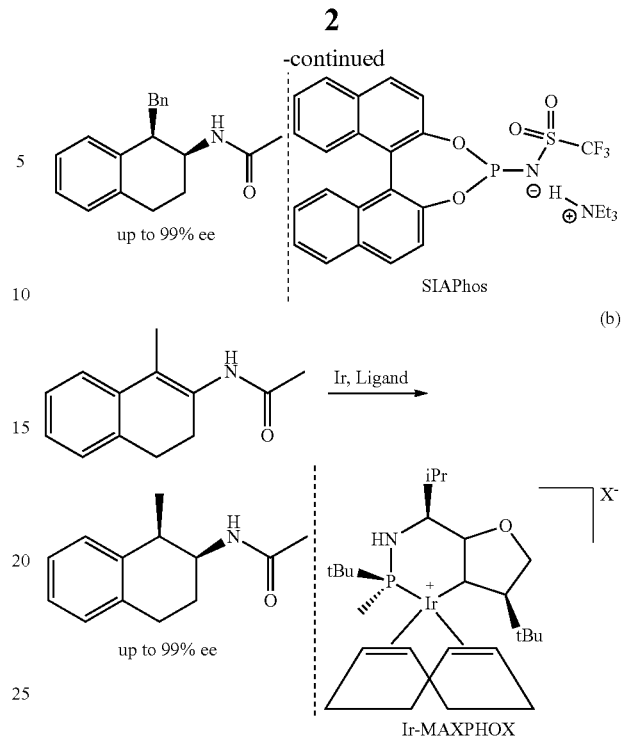

However, there is no report on the asymmetric hydrogenation of tetra-substituted α, β-alkyl cycloalkenamide. (as shown in the figure below, $R^1$, $R^2$ and $R^3$ are all alkyl)

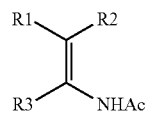

From the above research progress, it can be seen that although certain progress has been made in the asymmetric hydrogenation of enamide compounds, there are still many challenging hydrogenation substrates that cannot achieve satisfactory yield or enantioselectivity, and there are still many difficulties urgently need to break through, which is a very challenging subject.

BRIEF SUMMARY OF THE INVENTION

The technical problem to be solved herein is to provide a metal complex, intermediate, preparation method and application thereof which aim at deficiencies of existing catalysts for enamide hydrogenation catalyzation so as to synthesize chiral amides, such as small variety and low efficiency. The present invention prepared a metal complex by complexing chiral phosphine ligand with transition metal, which can be used as catalysts for asymmetric catalytic hydrogenation so as to efficiently catalyze and synthesize a series of chiral β-aryl amides with high optical purity (ee value>99%), especially asymmetrically catalyze hydrogenation of tetra-substituted enamide compounds so as to synthesize chiral amides at high optical purity (ee value reach more than 60%); and of which ligand carrying capacity (s/c) can reach up to 100,000, being greatly improved than the current technology and showing strong economic practicability.

The present invention solves the technical problems mentioned above through the following technical solutions.

The present invention provides a metal complex according to Formula I:

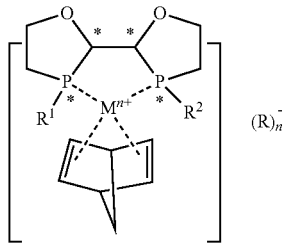

wherein, $R^1$ and $R^2$ are each independently hydrogen, $C_1$-$C_{10}$ alkyl, $C_1$-$C_4$ alkoxy, $C_3$-$C_{30}$ cycloalkyl, halogen or $C_6$-$C_{30}$ aryl;

$M^{n+}$ is a transition metal ion; n is 1, 2 or 3, which corresponds to the ion valence of the transition metal M;

the carbon atoms marked with * are all S configuration chiral carbons or all R configuration chiral carbons;

the P (phosphorus atom) marked with * are all S configuration chiral P or all R configuration chiral P.

In one embodiment, some groups of the metal complex according to Formula I are defined as follows, while the undefined groups are as described in any of the previous embodiments:

when $R^1$ or $R^2$ are each independently $C_1$-$C_{10}$ alkyl, the $C_1$-$C_{10}$ alkyl is $C_{1-6}$ alkyl; the $C_{1-6}$ alkyl is preferably each independently methyl, ethyl, n-propyl, iso-propyl, n-butyl, sec-butyl, iso-butyl, tert-butyl, n-pentyl, iso-pentyl, neo-pentyl or hexyl; more preferably is $C_{1-4}$ alkyl (for example, methyl, ethyl, n-propyl, iso-propyl, n-butyl, sec-butyl, iso-butyl or ten-butyl).

In one embodiment, some groups of the metal complex according to Formula I are defined as follows, while the undefined groups are as described in any of the previous embodiments:

when $R^1$ or $R^2$ are each independently $C_1$-$C_4$ alkoxy, the $C_1$-$C_4$ alkoxy is methoxy, ethoxy, n-propoxy, iso-propoxy, n-butoxy, sec-butoxy, iso-butoxy or tert-butoxy.

In one embodiment, some groups of the metal complex according to Formula I are defined as follows, and the undefined groups are as described in any of the previous embodiments:

when $R^1$ or $R^2$ are each independently $C_3$-$C_{30}$ cycloalkyl, the $C_3$-$C_{30}$ cycloalkyl is $C_3$-$C_8$ cycloalkyl (such as cyclopropanyl, cyclobutanyl, cyclopentyl, cyclohexyl, cycloheptyl or cyclooctyl).

In one embodiment, some groups of the metal complex according to Formula I are defined as follows, and the undefined groups are as described in any of the previous embodiments:

when $R^1$ or $R^2$ are each independently $C_6$-$C_{30}$ aryl, the $C_6$-$C_{30}$ aryl is $C_6$-$C_{14}$ aryl (for example, phenyl or naphthyl).

In one embodiment, some groups of the metal complex according to Formula I are defined as follows, and the undefined groups are as described in any of the previous embodiments:

when $R^1$ or $R^2$ are each independently halogen, the halogen is fluorine, chlorine, bromine or iodine.

In one embodiment, some groups of the metal complex according to Formula I are defined as follows, and the undefined groups are as described in any of the previous embodiments:

$R^1$ is the same as $R^2$.

In one embodiment, some groups of the metal complex according to Formula I are defined as follows, and the undefined groups are as described in any of the previous embodiments:

the transition metal ion $M^{n+}$ is preferably $Rh^+$, $Ru^{2+}$, $Ni^{2+}$, $Ir^{2+}$, $Pd^{2+}$, $Cu^{2+}$, $Pt^{2+}$, $Co^{2+}$ or $Au^{3+}$; preferably, $Ru^{2+}$ or $Rh^+$.

In one embodiment, some groups of the metal complex according to Formula I are defined as follows, and the undefined groups are as described in any of the previous embodiments:

the anion $R^-$ may be conventional anion in the art, such as $BF_4^-$, $SbF_6^-$, $TfO^-$, $B(C_6H_5)_4^-$, $B[3,5-(CF_3)_2C_6H_3]_4^-$ or $PF_6^-$; preferably, $BF_4^-$ or $PF_6^-$.

In one embodiment, some groups of the metal complex according to Formula I are defined as follows, and the undefined groups are as described in any of the previous embodiments:

the metal complex of Formula I is

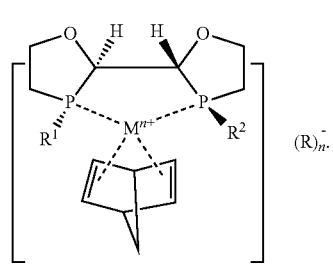

I-1

Some groups of the metal complex according to Formula I are defined as follows, and the undefined groups are as described in any of the previous embodiments:

the metal complex of Formula I is

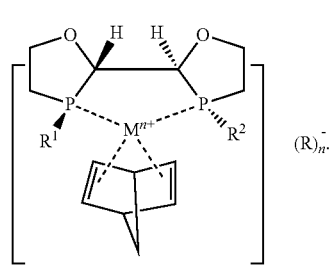

I-2

In one embodiment, the metal complex of Formula I is

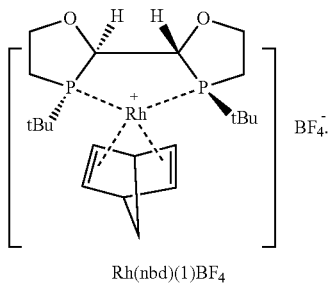

Rh(nbd)(1)BF$_4$

In one embodiment, the metal complex of Formula I is

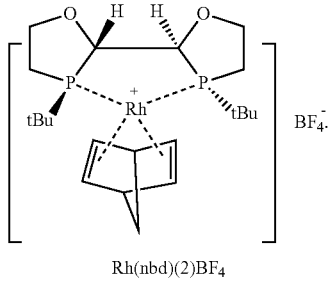

Rh(nbd)(2)BF$_4$

The present invention also provides the method for preparing the metal complex according to Formula I, which comprises the following steps: in an inert gas atmosphere, in the first organic solvent, the transition metal precursor according to Formula III and the ligand compound according to Formula II are subjected to the complexation reaction shown below to afford the metal complex according to Formula I;

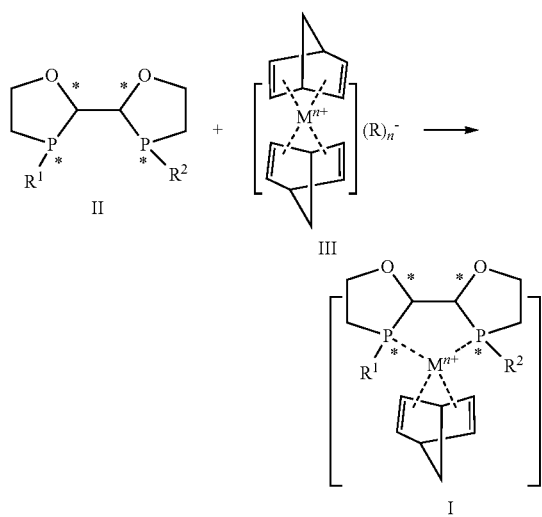

wherein, R$^1$, R$^2$, M$^{n+}$, R$^-$, n and "*" are all defined as described above.

In the method for preparing the metal complex according to Formula I, the operation and conditions of complexation reaction can be conventional operations and conditions in the art.

Wherein, the inert gas may be conventional inert gas in this type of reaction in the art, for example, argon and/or nitrogen.

Wherein, the first organic solvent may be conventional organic solvent in this type of reaction in the art, such as one or more of: ether solvents (for example, one or more of tetrahydrofuran, diethyl ether, and methyl tert-butyl ether MTBE), nitrile solvents (such as acetonitrile), halogenated alkane solvents (such as one or more of dichloromethane, 1,2-dichloroethane and chloroform), sulfoxide solvents (such as dimethyl sulfoxide DMSO) and amide solvents (for example, N,N-dimethylformamide DMF), preferably tetrahydrofuran.

The amount of the first organic solvent may be conventional amount in this type of reaction in the art, as long as the reaction would not be affected.

Wherein, the molar ratio of the transition metal precursor III of Formula III to the ligand compound of Formula II may be conventional molar ratio in this type of reaction in the art, the molar ratio of the transition metal precursor of Formula III to the ligand compound of Formula II is preferably 1:1.0 to 1:1.3 (for example, 1:1.1).

Wherein, the complexation reaction temperature may be conventional temperature in this type of reaction in the art, for example, −15° C. to 30° C. (for example, 0° C. to 25° C.).

Wherein, the progress of complexation reaction may be monitored by TLC or HPLC, and the end of the reaction is generally confirmed as the transition metal precursor of Formula III or the ligand compound of Formula II disappeared. The reaction time may be 0.1 to 1 hour (for example, 0.1 to 0.5 hour).

Wherein, the reaction further includes the post-treatment. The post-treatment may include the following operations: concentration, washing, and solvent removal. The concentration can be carried out by rotary evaporation, and the washing can be carried out with ether, for example, washing for once; after the solid is precipitated, the washing solvent may be directly poured out, and the remaining solvent may be drained by an oil pump or directly filtered off.

The method for preparing the metal complex according to Formula I may further include the following steps: in an inert gas atmosphere, in the second organic solvent, the compound according to Formula IV and the reducing agent are subjected to the reduction reaction shown below to obtain the compound II;

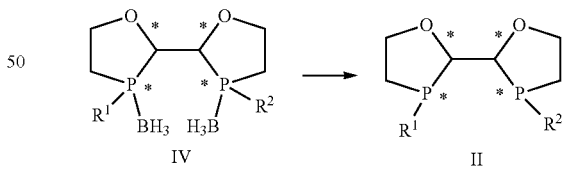

wherein, R$^1$, R$^2$ and "*" are all defined as described above.

The operation and conditions of the reduction reaction may be conventional operations and conditions in the art. Especially, the following conditions are chosen in the invention:

In the reduction reaction, the inert gas may be conventional inert gas in this type of reaction in the art, such as argon and/or nitrogen.

In the reduction reaction, the second organic solvent may be conventional organic solvent in this type of reaction in the art, such as one or more of: ether solvents (such as one or more of tetrahydrofuran, dioxane, diethyl ether, and methyl tert-butyl ether MTBE), aromatic solvents (such as toluene and/or benzene), nitrile solvents (such as acetonitrile), halogenated alkane solvents (such as one or more of dichloromethane, 1,2-dichloroethane and chloroform), sulfoxide solvents (such as dimethylsulfoxide DMSO) and amide solvents (such as N,N-dimethylformamide DMF), preferably toluene and/or tetrahydrofuran.

The amount of the second organic solvent may be conventional amount in this type of reaction in the art, as long as the reaction would not be affected.

In the reduction reaction, the reducing agent may be conventional reducing agent in this type of reaction in the art, such as one or more of triethylamine, diisopropylethylamine, tri-n-butylamine and 1,4-diazabicyclo[2.2.2]octane; preferably triethylamine and/or 1,4-diazabicyclo[2.2.2]octane.

In the reduction reaction, the molar ratio of the reducing agent to the compound IV may be conventional molar ratio in this type of reaction in the art, and the molar ratio of the reducing agent to the compound IV is preferably 10:1 to 1:1 (for example, 3:1).

In the reduction reaction, the reaction temperature may be conventional temperature in this type of reaction in the art, for example, 20° C. to 100° C. (for example, 60-80° C.).

In the reduction reaction, the progress of reaction may be monitored by TLC or HPLC, and the end of the reaction is generally confirmed as the compound of Formula IV disappeared. The reaction time may be 4-24 hours (for example, 12-16 hours).

The method for preparing the metal complex according to Formula I may further include the following steps: in an inert gas atmosphere, in the third organic solvent, in the presence of base, ligand and metal oxidant, the compound of Formula V and the compound of Formula V' are subjected to the dimerization coupling reaction shown below to obtain the compound IV;

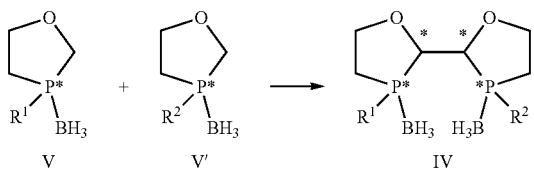

wherein, $R^1$ and $R^2$ are all defined as described above; the carbons marked with * are both S-configuration chiral carbons, or are both R-configuration chiral carbons; the two P marked with * are both S-configuration chiral P or are both R-configuration chiral P.

The operation and conditions of the coupling reaction may be conventional operations and conditions in the art. The present invention specifically chooses the following conditions:

In the coupling reaction, the inert gas may be conventional inert gas in this type of reaction in the art, such as argon and/or nitrogen.

In the coupling reaction, the third organic solvent may be conventional organic solvent in this type of reaction in the art, such as one or more of: ether solvents (such as one or more of tetrahydrofuran, dioxane, diethyl ether, and methyl tert-butyl ether MTBE), aromatic solvents (such as toluene and/or benzene), nitrile solvents (such as acetonitrile), halogenated alkane solvents (such as one or more of dichloromethane, 1,2-dichloroethane and chloroform), sulfoxide solvents (such as dimethyl sulfoxide DMSO) and amide solvents (such as N,N-dimethylformamide DMF), preferably tetrahydrofuran.

The amount of the third organic solvent may be conventional amount in this type of reaction in the art, as long as the reaction would not be affected.

In the coupling reaction, the base may be conventional base in this type of reaction in the art, such as one or more of n-butyllithium, sec-butyllithium, tert-butyllithium, lithium diisopropylamide, and diisopropylamine magnesium chloride lithium chloride complexes; preferably lithium diisopropyl amide and/or tert-butyllithium.

In the coupling reaction, the ligand may be conventional ligand in this type of reaction in the art, such as one or more of tetramethylethylenediamine (TMEDA), tetrahydrofuran (THF), hexamethylphosphoramide (HMPA) and 1,4-diazabicyclo[2,2,2]octane (DABCO); preferably tetramethylethylenediamine (TMEDA).

In the coupling reaction, the metal oxidizing agent may be conventional metal oxidizing agent in this type of reaction in the art, such as one or more of copper (II) chloride, iron (III) chloride, copper (II) pivalate, and copper(II) isobutyrate; preferably copper (II) chloride.

In the coupling reaction, the molar ratio of the base to the compound V may be conventional molar ratio in this type of reaction in the art, and the molar ratio of the base to the compound V is preferably 10:1 to 1:1 (for example, 1.5:1).

In the coupling reaction, the molar ratio of the ligand to the compound V may be conventional molar ratio in this type of reaction in the art, and the molar ratio of the ligand to the compound V is preferably 10:1 to 1:1 (for example, 1.5:1).

In the coupling reaction, the molar ratio of the metal oxidant to the compound V may be conventional molar ratio in this type of reaction in the art, for example, the molar ratio of the metal oxidant to the compound V is 10:1 to 1:1 (for example, 3:1).

In the coupling reaction, the reaction temperature may be conventional temperature in this type of reaction in the art, for example, −78° C. to 30° C.

In the coupling reaction, the progress of reaction may be monitored by TLC or HPLC. The end of the reaction is generally confirmed as the compound of Formula V disappeared.

The method for preparing the metal complex according to Formula I may further include the following steps: in an inert gas atmosphere, in the fourth organic solvent, in the presence of reducing agent and borane, the compound of Formula IV is subjected to the reduction-oxidation reaction shown below to obtain the compound V;

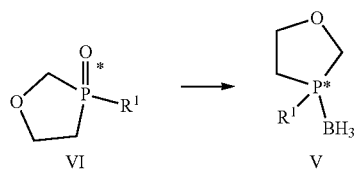

wherein, $R^1$ is defined as described above; P marked with * is S configuration chiral P or R configuration chiral P.

The operation and conditions of the reduction-oxidation reaction may be conventional operations and conditions in the art. The present invention specifically chooses the following conditions:

In the reduction-oxidation reaction, the inert gas may be conventional inert gas in this type of reaction in the art, such as argon and/or nitrogen.

In the reduction-oxidation reaction, the third organic solvent may be conventional organic solvent in this type of reaction in the art, such as one or more of ether solvents (such as one or more of tetrahydrofuran, dioxane, diethyl ether, and methyl tert-butyl ether MTBE), aromatic solvents (such as toluene and/or benzene), nitrile solvents (such as acetonitrile), halogenated alkane solvents (such as one or more of dichloromethane, 1,2-dichloroethane and chloroform), sulfoxide solvents (such as dimethyl sulfoxide DMSO) and amide solvents (such as N,N-dimethylformamide DMF), preferably tetrahydrofuran and/or dioxane.

In the reduction-oxidation reaction, the amount of the fourth organic solvent may be conventional amount in this type of reaction in the art, as long as the reaction would not be affected.

In the reduction-oxidation reaction, the reducing reagent may be conventional reducing reagent in this type of reaction in the art, such as "one or more of triethylamine, diisopropylethylamine and tri-n-butylamine", trichlorosilane and titanium tetraisopropoxide, or polymethoxyhydrosilane and titanium tetraisopropoxide; preferably polymethoxyhydrosilane and titanium tetraisopropoxide.

In the reduction-oxidation reaction, the molar ratio of the reducing reagent to the compound VI may be conventional molar ratio in this type of reaction in the art, and the molar ratio of the reducing reagent to the compound VI is preferably 10:1 to 1:1 (for example, 2.5:1 to 1.3:1).

In the reduction-oxidation reaction, the borane may be conventional borane in this type of reaction in the art, preferably tetrahydrofuran solution of borane (for example, 1M tetrahydrofuran solution).

In the reduction-oxidation reaction, the molar ratio of the borane to the compound VI may be conventional molar ratio in this type of reaction in the art, and the molar ratio of the metal oxidant to the compound VI is preferably 10:1 to 1:1 (for example, 2.5:1 to 1.2:1).

In the reduction-oxidation reaction, the reduction reaction temperature may be conventional temperature in this type of reaction in the art, for example, 20-80° C. (for example, 55-70° C.).

In the reduction-oxidation reaction, the oxidation reaction temperature may be conventional temperature in this type of reaction in the art, for example, 10-70° C. (for example, 15-40° C.).

In the reduction-oxidation reaction, the reaction progress may be monitored by TLC or HPLC. The end of the reaction is generally confirmed when the compound of Formula VI disappears and the reduction product V is afforded. The reduction reaction time is 2-24 hours (for example, 4-24 hours). The oxidation reaction time is 1-24 hours (for example, 2-24 hours).

The compound V' is obtained by the method for preparing compound V as described above.

The method for preparing the metal complex according to Formula I may further include the following steps: in the solvent, in the presence of oxidizing agent, the compound of Formula VII is subjected to the oxidation reaction shown below to obtain the compound VI;

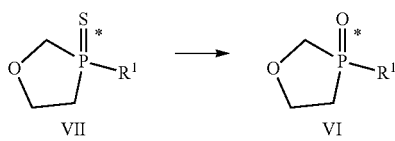

wherein, $R^1$ is defined as described above; P marked with * is S configuration chiral P or R configuration chiral P.

The operation and conditions of the oxidation reaction may be conventional operations and conditions in the art. The present invention specifically chooses the following conditions:

In the oxidation reaction, the solvent may be conventional solvent in this type of reaction in the art, such as one or more of water, alcohol solvents (such as methanol), ether solvents (such as one or more of tetrahydrofuran, dioxane, diethyl ether, and methyl tert-butyl ether MTBE), aromatic solvents (such as toluene and/or benzene), nitrile solvents (such as acetonitrile), halogenated alkane solvents (such as one or more of dichloromethane, 1,2-dichloroethane and chloroform), sulfoxide solvents (such as dimethyl sulfoxide DMSO) and amide solvents (such as N,N-dimethylformamide DMF), preferably water and methanol.

The amount of the solvent may be conventional amount in this type of reaction in the art, as long as the reaction would not be affected.

In the oxidation reaction, the oxidizing reagent may be conventional oxidizing reagent in this type of reaction in the art, such as hydrogen peroxide and/or m-chloroperoxybenzoic acid, preferably hydrogen peroxide.

In the oxidation reaction, the molar ratio of the oxidizing reagent to the compound VII may be conventional molar ratio in this type of reaction in the art, and the molar ratio of the oxidizing reagent to the compound VII is preferably 1:30 to 1:1 (for example, 1:2 to 1:1.87).

In the oxidation reaction, the reduction reaction temperature may be conventional temperature in this type of reaction in the art, for example, 0-80° C., preferably 15-40° C. (for example, 30° C.).

In the oxidation reaction, the reaction progress may be monitored by TLC or HPLC. The end of the reaction is generally confirmed as the compound of Formula VII disappeared.

The method for preparing the metal complex according to Formula I may further include the following steps: chiral separation of compound VII' to obtain compound VII;

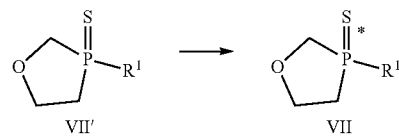

wherein, $R^1$ is defined as described above; the P marked with * in compound VII is S configuration chiral P or R configuration chiral P.

The operations and conditions of the chiral separation may be conventional operations and conditions in the art.

In the present invention, it is preferably: preparation column model: CHIRALPAK AD-H, Particle size=5 μm; Dimensions=4.6 mm*250 mm; mobile phase: isopropanol/n-hexane=5/95, flow rate: 1 ml per minute; detection wavelength: 210 nm.

The method for preparing the metal complex according to Formula I may further include the following steps: in an inert gas atmosphere, in the fifth organic solvent, in the presence of reducing agent and sulfur, the compound of Formula VI' is subject to the reduction-sulfurization reaction shown below to obtain the compound VII';

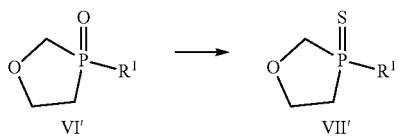

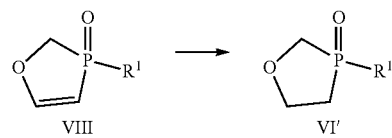

wherein, $R^1$ is defined as described above.

The operation and conditions of the reduction-sulfurization reaction may be conventional operations and conditions in the art. The present invention specifically chooses the following conditions:

In the reduction-sulfurization reaction, the inert gas may be conventional inert gas in this type of reaction in the art, such as argon and/or nitrogen.

In the reduction-sulfurization reaction, the fifth organic solvent may be conventional organic solvent in this type of reaction in the art, such as one or more of ether solvents (such as one or more of tetrahydrofuran, dioxane, diethyl ether, and methyl tert-butyl ether MTBE), aromatic solvents (such as toluene and/or benzene), nitrile solvents (such as acetonitrile), halogenated alkane solvents (such as one or more of dichloromethane, 1,2-dichloroethane and chloroform), sulfoxide solvents (such as dimethyl sulfoxide DMSO) and amide solvents (such as N,N-dimethylformamide DMF), preferably tetrahydrofuran and/or dioxane.

The amount of the fifth organic solvent may be conventional in this type of reaction in the art, as long as the reaction would not be affected.

In the reduction-sulfurization reaction, the reducing reagent may be conventional reducing reagent in this type of reaction in the art, such as "one or more of triethylamine, diisopropylethylamine and tri-n-butylamine", trichlorosilane and titanium tetraisopropoxide, or polymethoxyhydrosilane and titanium tetraisopropoxide; preferably polymethoxyhydrosilane and titanium tetraisopropoxide.

In the reduction-sulfurization reaction, the molar ratio of the reducing agent to the compound VI' may be conventional molar ratio in this type of reaction in the art, and the molar ratio of the reducing agent to the compound VI' is preferably 10:1 to 1:1 (for example, 2.5:1 to 1.4:1).

In the reduction-sulfurization reaction, the sulfur may be conventional sulfur in this type of reaction in the art, such as sulfur powder.

In the reduction-sulfurization reaction, the molar ratio of the sulfur to the compound VI' may be conventional molar ratio in this type of reaction in the art, and the molar ratio of the sulfur to the compound VI' is preferably 10:1 to 2:1 (for example, 2.5:1).

In the reduction-sulfurization reaction, the reduction reaction temperature may be conventional temperature in this type of reaction in the art, for example, 20-80° C. (for example, 55-70° C.).

In the reduction-sulfurization reaction, the reaction progress may be monitored by TLC or HPLC. The end of the reaction is generally confirmed as the compound of Formula VI' disappeared. The reduction reaction time is 2-24 hours (for example, 4-24 hours).

The method for preparing the metal complex according to Formula I may further include the following steps: in the sixth organic solvent, in the presence of reducing agent, the compound of Formula VIII is subjected to the reductive hydrogenation reaction as shown below to obtain the compound VI';

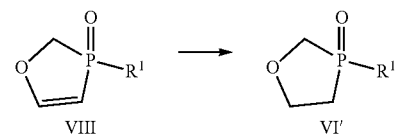

wherein, IV is defined as described above.

The operation and conditions of the reduction reaction may be conventional operations and conditions in the art. The present invention specifically chooses the following conditions:

In the reduction reaction, the sixth organic solvent may be conventional organic solvent in this type of reaction in the art, such as one or more of ester solvents (such as ethyl acetate), ether solvents (such as one or more of tetrahydrofuran, dioxane, diethyl ether, and methyl tert-butyl ether MTBE), aromatic solvents (such as toluene and/or benzene), nitrile solvents (such as acetonitrile), halogenated alkane solvents (such as one or more of dichloromethane, 1,2-dichloroethane and chloroform), sulfoxide solvents (such as dimethyl sulfoxide DMSO) and amide solvents (such as N,N-dimethylformamide DMF), preferably ethyl acetate.

The amount of the sixth organic solvent may be conventional amount in this type of reaction in the art, as long as the reaction would not be affected.

In the reduction reaction, the reducing reagent may be conventional reducing reagent in this type of reaction in the art, such as palladium catalyst and hydrogen; the palladium is, for example, palladium carbon and/or palladium hydroxide carbon (for example, 10% palladium carbon).

In the reduction reaction, the pressure of the hydrogen gas may be the conventional argon in this type of reaction in the art, for example, 15-750 psi (for example, 30-500 psi).

In the reduction reaction, the reduction reaction temperature may be conventional temperature in this type of reaction in the art, for example, 40° C. In the reduction reaction, the reaction progress may be monitored by TLC or HPLC. The end of the reaction is generally confirmed as the compound of Formula VIII disappeared.

The method for preparing the metal complex according to Formula I may further include the following steps: in the seventh organic solvent, in the presence of brominating reagent and base, the compound of Formula IX is subjected to the bromination-cyclization reaction shown below to obtain the compound VIII;

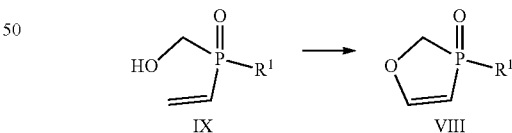

wherein, $R^1$ is defined as described above.

The operation and conditions of the bromination-cyclization reaction may be conventional operations and conditions in the art. The present invention specifically chooses the following conditions:

In the bromination-cyclization reaction, the seventh organic solvent may be conventional organic solvent in this type of reaction in the art, such as one or more of ether solvents (such as one or more of tetrahydrofuran, dioxane, diethyl ether, and methyl tert-butyl ether MTBE), aromatic solvents (such as toluene and/or benzene), nitrile solvents (such as acetonitrile), halogenated alkane solvents (such as one or more of dichloromethane, 1,2-dichloroethane and chloroform), sulfoxide solvents (such as dimethyl sulfoxide DMSO) and amide solvents (such as N,N-dimethylformamide DMF), preferably carbon tetrachloride and tetrahydrofuran.

The amount of the seventh organic solvent may be conventional in this type of reaction in the art, as long as the reaction would not be affected.

In the bromination-cyclization reaction, the bromination reagent may be conventional bromination reagent in this type of reaction in the art, such as liquid bromine.

In the bromination-cyclization reaction, the molar ratio of the bromination reagent to the compound IX may be conventional molar ratio in this type of reaction in the art, and the molar ratio of the bromination reagent to the compound IX is preferably 10:1 to 1:1 (for example, 2:1).

In the bromination-cyclization reaction, the base may be conventional base in this type of reaction in the art, such as one or more of sodium hydroxide, potassium hydroxide, sodium methoxide, lithium methoxide, sodium ethoxide, lithium ethoxide, sodium tert-butoxide and lithium tert-butoxide, preferably sodium tert-butoxide.

In the bromination-cyclization reaction, the molar ratio of the base to the compound IX may be conventional molar ratio in this type of reaction in the art, and the molar ratio of the base to the compound IX is preferably 10:1 to 2:1 (for example, 2:1).

In the bromination-cyclization reaction, the bromination reaction temperature may be conventional temperature in this type of reaction in the art, for example, 0-30° C.

In the bromination-cyclization reaction, the cyclization reaction temperature may be conventional temperature in this type of reaction in the art, for example, 0-30° C.

In the bromination-cyclization reaction, the reaction progress may be monitored by TLC or HPLC. The end of the reaction is generally confirmed as the compound of Formula IX disappeared. The reaction time is 2-24 hours (for example, 4-24 hours).

The method for preparing the metal complex according to Formula I may further include the following steps:
step 1) in the eighth organic solvent, phosphorus trichloride, MgR$^1$Cl and vinylmagnesium bromide was subjected to alkylation reaction;
step 2) water was reacted with the reaction system of step 1);
step 3) the base and formaldehyde were reacted with the reaction system of step 2) to obtain the compound IX;

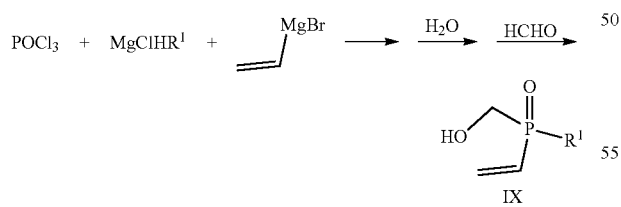

wherein, IV is defined as described above.

The operation and conditions of the reaction may be conventional operations and conditions in the art. Especially, the following conditions are chosen in present invention:

Wherein, the eighth organic solvent may be conventional organic solvent in this type of reaction in the art, such as one or more of: ether solvents (such as one or more of tetrahydrofuran, dioxane, diethyl ether, and methyl tert-butyl ether MTBE), aromatic solvents (such as toluene and/or benzene), nitrile solvents (such as acetonitrile), halogenated alkane solvents (such as one or more of dichloromethane, 1,2-dichloroethane and chloroform), sulfoxide solvents (such as dimethyl sulfoxide DMSO) and amide solvents (such as N,N-dimethylformamide DMF), preferably tetrahydrofuran and/or dioxane.

The amount of the eighth organic solvent may be conventional in this type of reaction in the art, so as not to affect the reaction.

Wherein, the molar ratio of the MgR$^1$Cl to the phosphorus trichloride may be conventional molar ratio in this type of reaction in the art, and the molar ratio of the MgR$^1$Cl to the phosphorus trichloride is preferably 1.2:1 to 0.8:1 (for example, 1:1).

Wherein, the molar ratio of the vinyl magnesium bromide to the phosphorus trichloride may be conventional molar ratio in this type of reaction in the art, and the molar ratio of the vinyl magnesium bromide to the phosphorus trichloride is preferably 1.2:1 to 0.8:1 (for example, 1:1).

Wherein, the molar ratio of the water to the phosphorus trichloride may be conventional molar ratio in this type of reaction in the art, and the molar ratio of the water to the phosphorus trichloride is preferably 10:1 to 3:1 (for example, 7.6:1).

Wherein, the molar ratio of the formaldehyde to the phosphorus trichloride may be conventional molar ratio in this type of reaction in the art, and the molar ratio of the formaldehyde to the phosphorus trichloride is preferably 10:1 to 3:1 (for example, 2:1).

Wherein, the base may be conventional base in this type of reaction in the art, such as sodium hydroxide and/or potassium hydroxide.

Wherein, the molar ratio of the base to the phosphorus trichloride may be conventional molar ratio in this type of reaction in the art. For example, the molar ratio of the base to the phosphorus trichloride is preferably 10:1 to 1:1 (for example, 2:1).

Wherein, the reaction temperature may be conventional temperature in this type of reaction in the art, for example, −50° C.~60° C. (for example, 15~45° C.).

Wherein, the reaction progress may be monitored by TLC, HPLC or $^{31}$P-NMR.

The present invention also provides a compound according to Formula II,

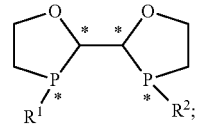

wherein, R$^1$, R$^2$ and "*" are all defined as described above.

In one embodiment of the present invention, the compound according to Formula II shows any of the following structures:

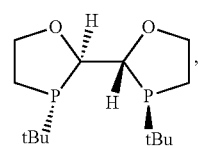

-continued

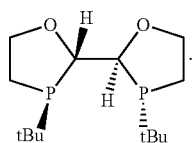

The present invention also provides a compound according to Formula IV,

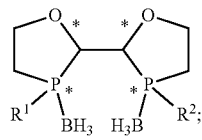

wherein, $R^1$, $R^2$ and "*" are all defined as described above.

In one embodiment of the present invention, the compound according to Formula IV is any of the following structures:

h-1

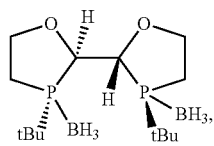

h-2

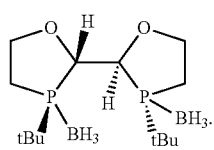

The present invention also provides a compound according to Formula V,

V

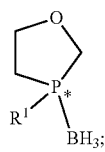

wherein, $R^1$ and "*" are both defined as described above.

In one embodiment of the present invention, the compound according to Formula V is any of the following structures:

g-1

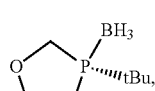

g-2

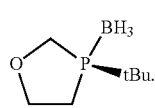

The present invention also provides a compound according to Formula VI,

VI

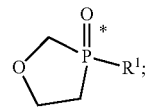

wherein, $R^1$ and "*" are both defined as described above.

In one embodiment of the present invention, the compound according to Formula VI is any of the following structures:

f-1

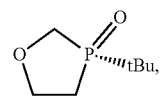

f-2

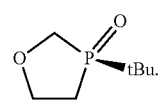

The present invention also provides a compound according to Formula VII,

VII

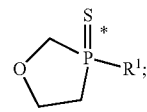

wherein, $R^1$ and "*" are both defined as described above.

In one embodiment of the present invention, the compound according to Formula VII is any of the following structures:

e-1

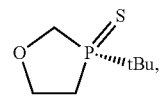

e-2

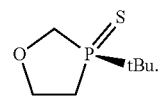

The present invention also provides a compound according to Formula VII',

VII'

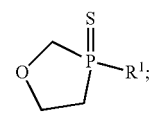

wherein, $R^1$ is defined as described above.

In one embodiment of the present invention, the compound according to Formula VII' is any of the following structures:

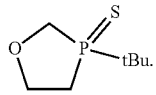

d

The present invention also provides a compound according to Formula VI',

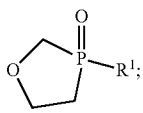

VI' wherein, R¹ is defined as described above.

In one embodiment of the present invention, the compound according to Formula VI' is any of the following structures:

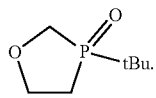

c

The present invention also provides a compound according to Formula VIII,

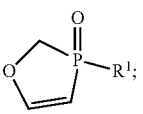

VIII wherein, R¹ is defined as described above.

In one embodiment of the present invention, the compound according to Formula VIII is any of the following structures:

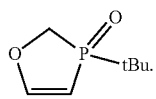

b

The present invention also provides a compound according to Formula IX,

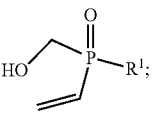

IX wherein, R¹ is defined as described above.

In one embodiment of the present invention, the compound according to Formula IX is any of the following structures:

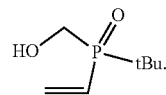

a

The present invention provides a method for preparing compound II, which comprises the following steps: in an inert gas atmosphere, in the second organic solvent, the compound according to Formula IV and the reducing agent are subjected to reduction reaction as shown below to obtain the compound II;

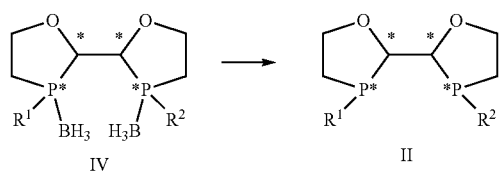

wherein, R¹, R² and "*" are all defined as described above.

In the method for preparing compound II, the operation and conditions of the reaction are the same as those described above.

The present invention provides a method for preparing compound IV, which includes the following steps: in an inert gas atmosphere, in the third organic solvent, in the presence of base, ligand and metal oxidant, the compound according to Formula V is subjected to dimerization coupling reaction shown below to obtain the compound IV;

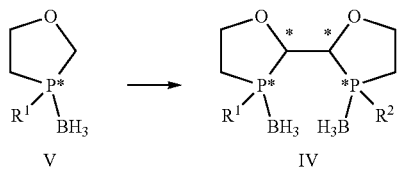

wherein, R¹ and R² are defined as described above, and R¹ and R² are the same; the carbons marked with * are both chiral carbons in S configuration or both chiral carbons in R configuration; the two Ps marked with * are both chiral P in S configuration or all chiral P in R configuration.

In the method for preparing compound IV, the operation and conditions of the reaction are the same as those described above.

The present invention provides a method for preparing compound V, which includes the following steps: in an inert gas atmosphere, in the fourth organic solvent, in the presence of reducing agent and borane, the compound according to Formula VI is subjected to reduction-oxidation reaction shown below to obtain the compound V;

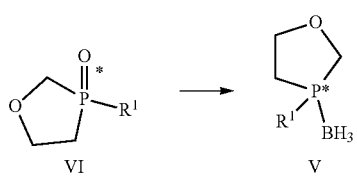

wherein, $R^1$ is defined as described above; P marked with * is chiral P in S configuration or chiral P in R configuration.

In the method for preparing compound V, the operation and conditions of the reaction are the same as those described above.

The present invention provides a method for preparing compound VI, which includes the following steps: in the solvent, in the presence of oxidizing reagent, the compound according to Formula VII is subjected to the oxidation reaction shown below to obtain the compound VI;

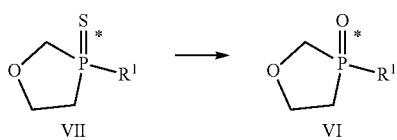

wherein, $R^1$ is defined as described above; P marked with * is chiral P in S configuration or chiral P in R configuration.

In the method for preparing compound VI, the operation and conditions of the reaction are the same as those described above.

The present invention provides a method for preparing compound VII, which includes the following step: chiral separating compound VII' to obtain compound VII;

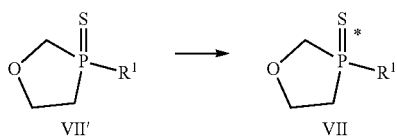

wherein, $R^1$ is defined as described above; P marked with * is chiral P in S configuration or chiral P in R configuration.

In the method for preparing compound VII, the operation and conditions of the reaction are the same as those described above.

The present invention provides a preparation method of compound VII', which includes the following steps: in an inert gas atmosphere, in the fifth organic solvent, in the presence of reducing agent and sulfur, the compound according to Formula VI' is subjected to the reduction-sulfurization reaction shown below to obtain the compound VII';

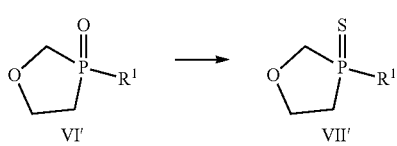

wherein, $R^1$ is defined as described above.

In the method for preparing compound VII', the operation and conditions of the reaction are the same as those described above.

The present invention provides a method for preparing compound VI', which includes the following steps: in the sixth organic solvent, in the presence of reducing agent, the compound according to Formula VIII is subjected to the reductive hydrogenation reaction shown below to obtain the compound VI';

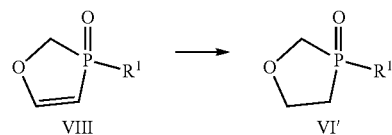

wherein, $R^1$ is defined as described above.

In the preparation method of compound VI', the operation and conditions of the reaction are the same as those described above.

The present invention provides a preparation method of compound VIII, which includes the following steps: in the seventh organic solvent, in the presence of bromination reagent and base, the compound according to Formula IX is subjected to the bromination-cyclization reaction as shown below to obtain the compound VIII;

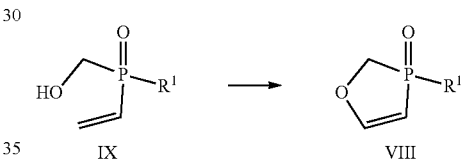

wherein, $R^1$ is defined as described above.

In the method for preparing compound VIII, the operation and conditions of the reaction are the same as those described above.

The present invention provides a preparation method of compound IX, which includes the following steps:

step 1) in the eighth organic solvent, phosphorus trichloride was reacted with $MgR^1Cl$ and vinylmagnesium bromide;

step 2) water was reacted with the reaction system of step 1);

step 3) base and formaldehyde was reacted with the reaction system of step 2) to obtain the compound IX;

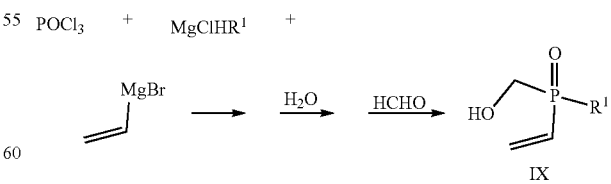

wherein, $R^1$ is defined as described above.

In the method for preparing compound IX, the operation and conditions of the reaction are the same as those described above.

The present invention provides an application of the metal complex of Formula I in the asymmetric catalytic hydrogenation reaction; which comprises the following steps: in the organic solvent, in a hydrogen atmosphere and the presence of the metal complex of Formula I, the compound A containing the structure of

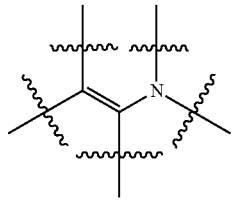 [SMILES: *C(*)=C(*)N(*)*]

is subjected to the asymmetric hydrogenation reduction reaction to obtain the corresponding compound B;

wherein, when the metal complex of Formula I is

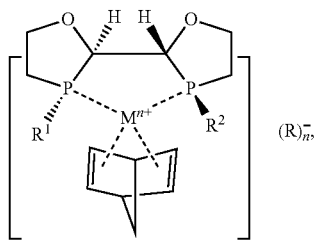
I-1 the predominant configuration of compound B comprises the structure of

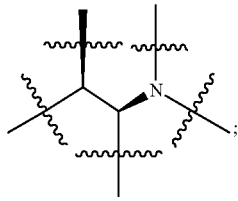
B-1
;

when the metal complex according to Formula I is

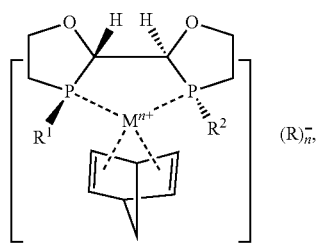
I-2 the predominant configuration of compound B comprises the structure of

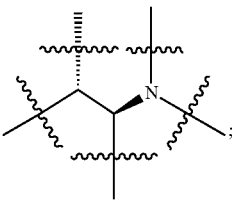
B-2
;

wherein, $R^1$, $R^2$ and n are all defined as above.

In the application, the metal complex of Formula I is used as catalyst.

In the application, the metal complex of Formula I can be generated in situ from the transition metal precursor of Formula III and the ligand compound of Formula II.

In one embodiment, ee value of the predominant configuration is >65%, preferably >95%; more preferably >99%.

In one embodiment, the compound A containing the structure of is

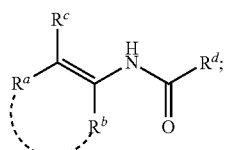

preferably of Formula A-1:

A-1

$$\underset{R^a}{\overset{R^c}{\diagdown}}{=}\underset{R^b}{\overset{}{\diagup}}\underset{}{\overset{H}{N}}\underset{O}{\overset{}{\diagdown}}R^d;$$

wherein, the dotted line is absent or ring structure;

$R^a$, $R^b$ and $R^c$ are each independently H, —COOH, —OH, —CN, optionally substituted alkyl-oxy, optionally substituted alkyl-oxy-carbonyl, optionally substituted alkyl-carbonyl-oxy, optionally substituted alkyl or cycloalkyl, optionally substituted heterocycloalkyl, optionally substituted aryl or optionally substituted heteroaryl;

or $R^a$ and $R^b$, together with the carbon atom to which they are connected, form optionally substituted cycloalkene or optionally substituted heterocycloalkene;

$R^d$ is independently optionally substituted alkyl or cycloalkyl, optionally substituted heterocycloalkyl, optionally substituted aryl or optionally substituted heteroaryl.

Wherein, the "optionally substituted" may be unsubstituted or substituted by the conventional substituents in the art so as not to affect the reaction; for example, substituted by the following groups: halogen (for example, F, Cl, Br or I), haloalkyl, —OH, —CN, alkyl-oxy, alkyl-S—, carboxy, ester group, carbonyl, amido, optionally substituted amino-sulfonyl or optionally substituted phenyl; the number of "substitution" is not limited; when it is optionally substituted cycloalkenyl, optionally substituted heterocycloalkenyl, optionally substituted cycloalkyl, optionally substituted heterocycloalkyl, optionally substituted aryl or optionally substituted heteroaryl, the "substituted" may be form fused ring with the cycloalkene, heterocycloalkene, cycloalkyl, heterocycloalkyl, aryl or heteroaryl.

In one embodiment, in the compound A, the alkyl is $C_1$-$C_{10}$ alkyl (such as $C_1$-$C_6$ alkyl, another example is methyl, ethyl, n-propyl, iso-propyl, n-butyl, sec-butyl, iso-butyl, tert-butyl, n-pentyl, iso-pentyl, neo-pentyl, or hexyl).

In one embodiment, in the compound A, in the alkyl-oxy, alkyl-oxy-carbonyl and alkyl-carbonyl-oxy, the alkyl groups are each independently alkyl defined as above.

In one embodiment, in the compound A, the cycloalkyl is $C_3$-$C_{30}$ cycloalkyl (for example, $C_3$-$C_8$ cycloalkyl, another example is cyclopentyl or cyclohexyl).

In one embodiment, in the compound A, the heterocycloalkyl is "4-7 membered heterocycloalkyl with 1-3 heteroatoms selected from one or more of N, O and S" (for example, "5-6 membered heterocycloalkyl with 1 to 2 heteroatoms selected from N and/or O").

In one embodiment, in the compound A, the aryl is $C_6$-$C_{14}$ aryl (for example, phenyl).

In one embodiment, in the compound A, the heteroaryl is "$C_1$-$C_{10}$ heteroaryl with 1-4 heteroatoms selected from one or more of N, O and S" (for example, "$C_3$-$C_9$ heteroaryl with 1 to 2 heteroatoms selected from N").

In one embodiment, in the compound A, the cycloalkene is $C_5$-$C_7$ cycloalkene (for example, cyclopentene or cyclohexene).

In one embodiment, in the compound A, the heterocycloalkene is "5-7 membered heterocycloalkene with 1 to 2 heteroatoms selected from one or more of N, O and S".

In one embodiment, certain groups of the compound A are defined as follows, and undefined groups are as described in any of the preceding embodiments: when $R^a$, $R^b$ or $R^c$ is optionally substituted alkyl, the optionally substituted alkyl is $C_1$-$C_6$ alkyl, such as methyl, ethyl, n-propyl, iso-propyl, n-butyl, sec-butyl, iso-butyl, tert-butyl, n-pentyl, iso-pentyl, neo-pentyl, or hexyl, or methyl.

In one embodiment, some groups of the compound A are defined as follows, and undefined groups are as described in any of the preceding embodiments: $R^a$, $R^b$ or $R^c$ is —COOH or optionally substituted alkyl-oxy-carbonyl, the optionally substituted alkyl-oxy-carbonyl is preferably $C_1$-$C_6$ alkyl-oxy-carbonyl (for example, methyl-oxy-carbonyl).

In one embodiment, some groups of the compound A are defined as follows, and undefined groups are as described in any of the preceding embodiments: when $R^a$, $R^b$ or $R^c$ is optionally substituted aryl, the optionally substituted aryl is phenyl or halogen-substituted phenyl (for example, bromophenyl

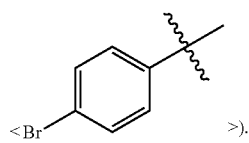 [SMILES: *c1ccc(Br)cc1]

).

In one embodiment, some groups of the compound A are defined as follows, and undefined groups are as described in any of the preceding embodiments: when "$R^a$ and $R^b$, together with the carbon atom to which they are connected, form optionally substituted cycloalkene", the "optionally substituted cycloalkene" is benzocyclohexene (for example

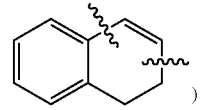

)

or cyclohexene.

In one embodiment, some groups of the compound A are defined as follows, and undefined groups are as described in any of the preceding embodiments: when $R^d$ is optionally substituted alkyl, the optionally substituted alkyl is $C_1$-$C_6$ alkyl, (such as methyl, ethyl, n-propyl, iso-propyl, n-butyl, sec-butyl, iso-butyl, tert-butyl, n-pentyl, iso-pentyl, neo-pentyl, or hexyl, another example is methyl).

In one embodiment, some groups of the compound A are defined as follows, and undefined groups are as described in any of the preceding embodiments: $R^d$ is $C_1$-$C_{10}$ alkyl (for example, $C_1$-$C_6$ alkyl, another example is methyl, ethyl, n-propyl, iso-propyl, n-butyl, sec-butyl, iso-butyl, tert-butyl, n-pentyl, iso-pentyl, neo-pentyl, or hexyl; preferably is methyl), and $R^b$ is optionally substituted aryl; that is, α-arylamide compound, for example

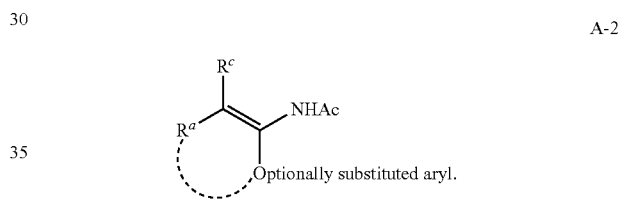

A-2

In one embodiment, some groups of the compound A are defined as follows, and undefined groups are as described in any of the preceding embodiments: $R^d$ is independently $C_1$-$C_{10}$ alkyl (for example, $C_1$-$C_6$ alkyl, another example is methyl, ethyl, n-propyl, iso-propyl, n-butyl, sec-butyl, iso-butyl, tert-butyl, n-pentyl, iso-pentyl, neo-pentyl, or hexyl; preferably is methyl), and $R^b$ is optionally substituted alkyl-oxy-carbonyl; that is, α-dehydroamino acid derivative, for example

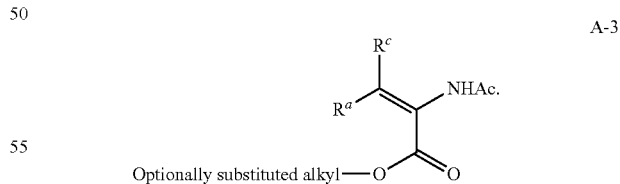

A-3

In one embodiment, some groups of the compound A are defined as follows, and undefined groups are as described in any of the preceding embodiments: $R^d$ is independently $C_1$-$C_{10}$ alkyl (for example, $C_1$-$C_6$ alkyl, another example is methyl, ethyl, n-propyl, iso-propyl, n-butyl, sec-butyl, iso-butyl, tert-butyl, n-pentyl, iso-pentyl, neo-pentyl, or hexyl; preferably is methyl), $R^a$ or $R^c$ are each independently optionally substituted alkyl-oxy-carbonyl; that is, β-(acetamido) acrylate, such as

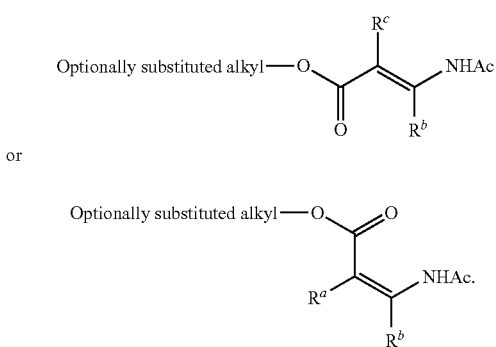

The application of the metal complex of Formula I in catalytic hydrogenation, wherein the compound A and the corresponding compound B-1 may be selected from the following compounds:

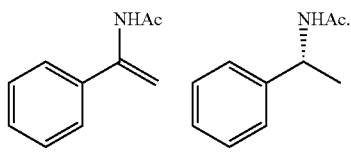

The compound A and corresponding compound B-2 may be selected from the following compounds:

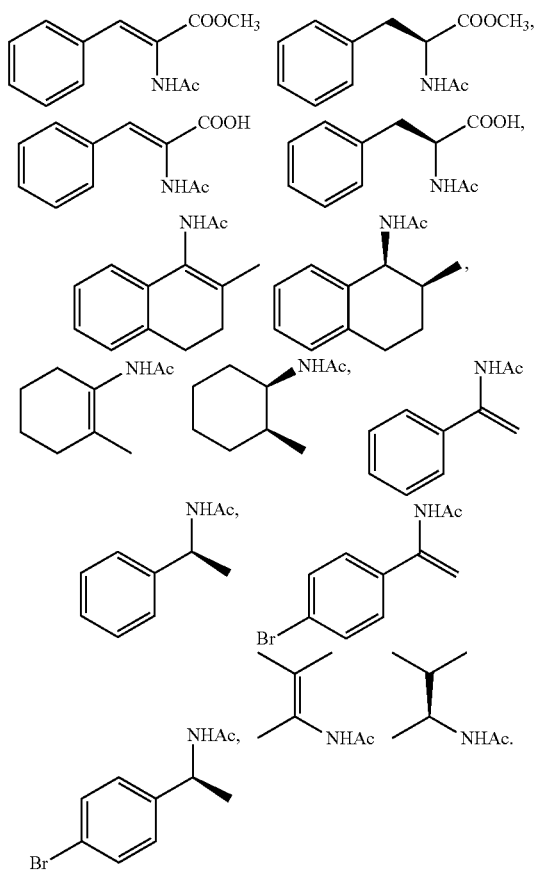

The application of the metal complex of Formula I in catalytic hydrogenation, wherein the organic solvent may be conventional solvent in this type of reaction in the art, such as one or more of ester solvents (such as ethyl acetate), ether solvents (for example, one or more of tetrahydrofuran, dioxane, diethyl ether, and methyl tert-butyl ether MTBE), aromatic solvents (such as toluene and/or benzene), nitrile solvents (such as acetonitrile), halogenated alkane solvents (such as one or more of dichloromethane, 1,2-dichloroethane and chloroform), sulfoxide solvents (such as dimethyl sulfoxide DMSO) and amide solvents (for example, N,N-dimethylformamide DMF), preferably ethyl acetate.

The amount of the organic solvent may be the conventional amount in this type of reaction in the art, so as not to affect the reaction.

Wherein, the molar ratio of the compound A to the metal complex according to Formula I may be conventional molar ratio in this type of reaction in the art, and preferably 100:1 to 100,000:1 in the present invention (for example, 200:1).

Wherein, the pressure of the hydrogen may be conventional pressure in this type of reaction in the art, for example, 750 psi.

Wherein, the reduction reaction temperature may be conventional temperature in this type of reaction in the art, for example, 20-100° C. (for example, 20-80° C., and for example 50° C.).

Wherein, the reaction progress may be monitored by TLC, HPLC, LC-MS or GC-MS. The end of the reaction is generally confirmed when the substrate disappears. The reaction time may be 4-24 hours (for example, 12-18 hours).

In the application, after the reduction reaction is completed, post-treatment steps may also be included. The post-treatment steps may include the following operations: removing hydrogen gas, filtering, washing, concentrating, and removing the solvent. The filtering can be carried out by using millipore membrane filter to remove metal ions; the washing can be carried out in sequence with water and saturated sodium chloride solution; the concentration can be carried out by rotary evaporation; and the solvent removal can be carried out by an oil pump.

In the present invention, the room temperature may be conventional room temperature as defined in the art, preferably 5-30° C.

Group Definition

In the present invention, "$C_1$-$C_{10}$ alkyl" refers to linear or branched saturated aliphatic hydrocarbon groups containing up to 10 carbon atoms, such as methyl, ethyl, propyl, iso-propyl, butyl, iso-butyl, tert-butyl, pentyl, iso-pentyl, neo-pentyl, hexyl, heptyl, iso-heptyl, octyl and iso-octyl.

In the present invention, the term "$C_1$-$C_6$ alkyl" is preferably each independently methyl, ethyl, propyl, butyl, pentyl or hexyl; wherein, propyl is $C_3$ alkyl (including isomers, such as n-propyl or iso-propyl); butyl is $C_4$ alkyl (including isomers, such as n-butyl, sec-butyl, iso-butyl or tert-butyl); pentyl is $C_5$ alkyl (including isomers, such as n-pentyl <for example,

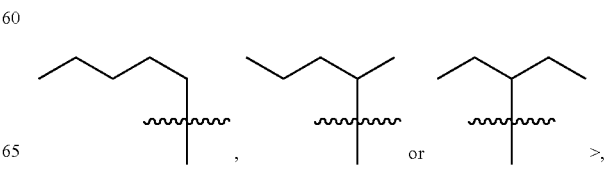

iso-pentyl <for example

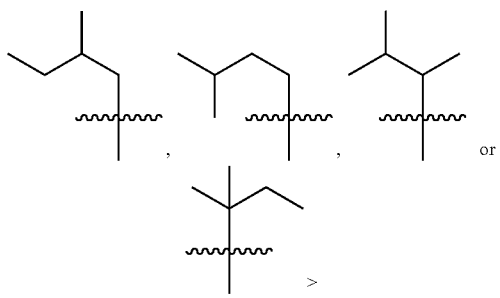

, , or or neo-pentyl <for example

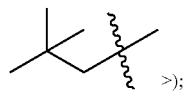

>);

hexyl is $C_6$ alkyl (including isomers, such as n-hexyl).

In the present invention, the term "$C_1$-$C_4$ alkyl" is preferably each independently methyl, ethyl, n-propyl, iso-propyl, n-butyl, sec-butyl, iso-butyl or tert-butyl.

Similarly, "$C_1$-$C_{10}$ alkoxy" or "$C_1$-$C_{10}$ alkyl-oxy" refers to alkyl as defined above connected through oxygen atom, such as methoxy, ethoxy, n-propoxy, iso-propoxy, n-butoxy, iso-butoxy or tert-butoxy, etc.

In the present invention, halogen includes F, Cl, Br or I.

In the present invention, "aryl" refers to substituent having the properties of aromatic ring structure, such as $C_6$-$C_{30}$ aryl. The aryl groups can be used in the present invention include, but are not limited to: phenyl, naphthyl, anthryl, and the like. In the present invention, aryl include unsubstituted or substituted aryl, where substitution refers to one or more hydrogen atoms on the group are substituted by substituent selected from the group consisting of $C_1$-$C_4$ alkyl, $C_3$-$C_{10}$ cycloalkyl, halogen, hydroxy, carboxy, aldehyde, acyl, amine, —$NR^3R^4$, wherein $R^3$ and $R^4$ are each H or $C_1$-$C_4$ alkyl or $C_1$-$C_4$ haloalkyl. Representative aryl include aryl with electron-donating and/or electron-withdrawing substituents, such as p-tolyl, p-methoxyphenyl, p-chlorophenyl and the like. Similarly, "arylalkyl" refers to substituent in which aryl and alkyl are connected, such as phenylmethyl, phenylethyl, phenylpropyl and the like. When aryl is used as substituent in a substituent, it is not further substituted.

Similarly, "heteroaryl" refers to aryl containing one or more heteroatoms selected from N, O, or S. In a specific embodiment, the "heteroaryl" in the present invention contains 6-30 carbon atoms and has at least one 5-8 membered heterocyclic ring containing 1-3 heteroatoms independently selected from O, N or S.

In the present invention, the number of the term "substitution" may be one or more <for example, 2, 3, 4 or 5>. When there are multiple "substitutions", the "substitutions" are the same or different.

In the present invention, the position of the term "substitution" may be any position unless otherwise specified.

Those skilled in the art could understand that according to the conventions used in the art, the " ⌇ " used in the structural formula of the group described in this application means that the corresponding group is connected to other fragments or groups in the compound through this site.

On the basis of not violating common knowledge in the field, the above-mentioned preferred conditions may be combined arbitrarily to obtain preferred embodiments of the present invention.

The reagents and raw materials used in the present invention are all commercially available.

The positive and progressive effects of the present invention are: 1. the metal complex according to Formula I obtained by complexing the chiral phosphine ligand of the present invention with transition metal may be used as catalyst for asymmetric catalytic hydrogenation reactions;

2. the metal complex according to Formula I of the present invention can efficiently catalyze and synthesize a series of chiral β-aryl amides at high optical purity (ee value>99%), especially asymmetric catalyze and hydrogenate tetrasubstituted enamide compounds, synthesize chiral amides with high optical purity (ee value up to 60%), and the carrying capacity of ligand (s/c) can reach 100,000, which is much higher than the prior art, and has strong economic practicality.

EMBODIMENTS FOR CARRYING OUT THE INVENTION

Figure 1:
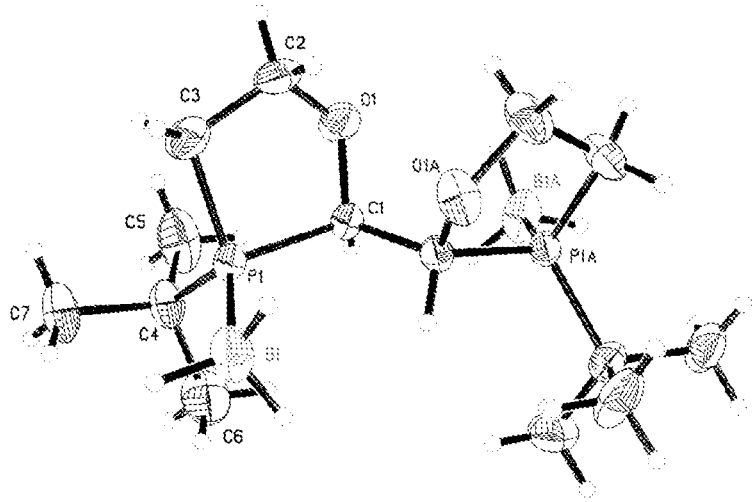
FIG. 1 is the single crystal X-ray diffraction of compound h-1.
Figure 2:
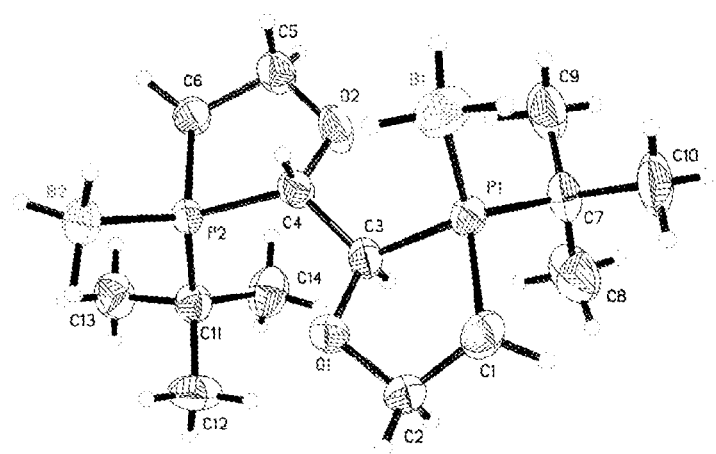
FIG. 2 is the single crystal X-ray diffraction of compound h-3.

The present invention will be further explained by examples below, but the present invention is not limited to the scope of the described examples. In the following examples, the experimental methods without specific conditions are selected according to conventional methods and conditions, or according to the manual of product.

Example 1

The example uses the preparation of (2R,2'R, 3S, 3'S)-3, 3'-di-t-butyl-2,2'-bis([1,3]oxaphospholanyl) (1) and its metal complex {(norbornadiene) [(2R,2'R,3 S,3'S)-3,3'-di-tert-butyl-2,2'-bis([1,3]oxaphospholanyl)]} rhodium tetrafluoroborate, i.e, Rh(nbd)(1)$BF_4$ (the reaction route is shown below) as an example to illustrate in detail the preparation method of the chiral bisphosphine ligand and its metal rhodium complex of the present invention, the reaction route is as follows:

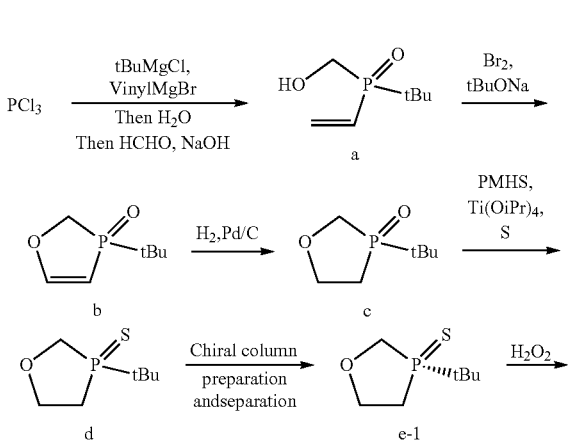

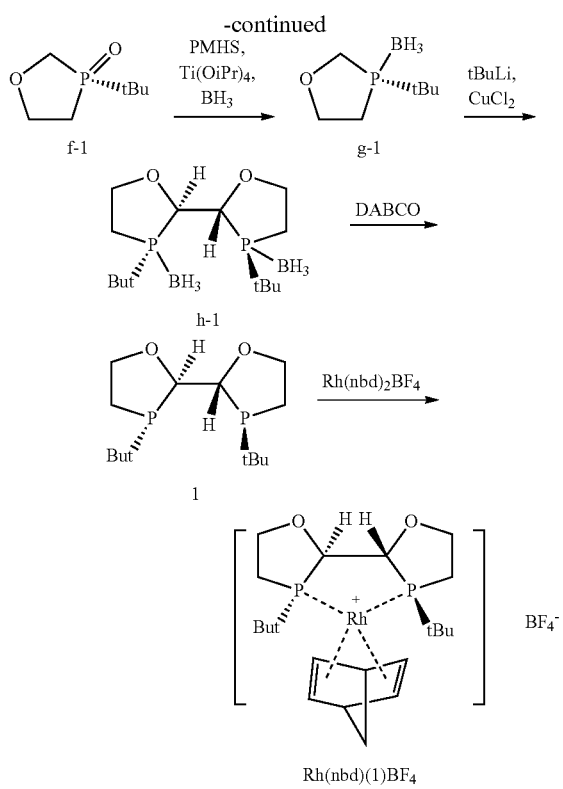

1. Preparation of tert-butyl (hydroxymethyl) (vinyl) phosphine oxide (a)

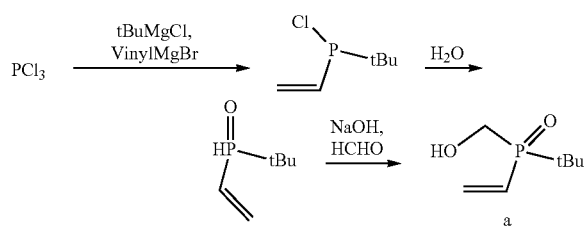

A 1000 mL four-necked flask was dried with baking gun and protected at nitrogen atmosphere. Thermowell and a low-temperature thermometer were inserted into one neck of the flask, a mechanical stirring device was inserted into another neck, and constant pressure dropping funnel was installed into the rest neck of the flask. The system was replaced with nitrogen for 3-5 times. 10 mL of $PCl_3$ was carefully drawn with syringe and dropped into pear-shaped bottle until the analytical balance showed 20 g (145.6 mmol, 1 equivalent), then the syringe was taken out. Under the protection of nitrogen, 40 mL of THF refluxed for three hours with sodium wire was added to dissolve, and the mixture was poured into the four-necked flask. 15 mL of tetrahydrofuran was added for rinsing the pear-shaped flask and transferred to the four-necked flask for 3 times.

The device was placed in an ice bath at −50° C., 176.9 mL (176.9 mmol, 1 equivalent) of tert-butylmagnesium chloride was drawn with syringe, injected into constant pressure dropping funnel to slowly add dropwise. The ice bath device was removed after dripping and warmed to the room temperature. After the temperature was stabilized, the mixture was reacted for 2 h. $^{31}$P-NMR was used to detect the reaction. When the reaction was completed, the product was proceed directly to the next step without separation.

The device was placed in an ice bath at −50° C., 154.9 mL (154.9 mmol, 1.1 equivalents) of vinylmagnesium bromide was drawed with syringe, injected into constant pressure dropping funnel to slowly add dropwise. The ice bath device was removed after dripping and warmed to the room temperature. After the temperature was stabilized, the mixture was reacted for 2 h. $^{31}$P-NMR was used to detect the reaction. When the reaction was completed, the product was proceed directly to the next step without separation.

A certain amount of deionized water was added into the container and sealed. Nitrogen was injected into the container to remove trace oxygen dissolved in the water. 20 mL of oxygen-free deionized water was drawed with syringe and injected into constant pressure dropping funnel, and slowly added dropwise. The device was put in an oil bath at 45° C. for 3 h (or 20 h at room temperature) after dripping. $^{31}$P-NMR was used to detect the reaction. When the reaction was completed, the product was proceed directly to the next step without separation.

Saturated sodium hydroxide solution containing 29 g of NaOH (725 mmol, 5 equivalents) which was configured with oxygen-free deionized water and blown with part of nitrogen was added into container. Under nitrogen atmosphere, 100 mL of formaldehyde solution (1233 mmol, 10 equivalents) and newly prepared NaOH solution were drawed using syringe, injected into constant pressure dropping funnel, and slowly dropped in an ice bath at −20° C. After addition, the device was warmed to room temperature, and then was put in an 50° C. oil bath for 3 h. TLC (developing solvent: ethyl acetate and methanol with volume ratio of 10:1, potassium permanganate as color developer) was used to detect the reaction. Post-treatment was performed after the reaction was completed.

The device was cooled to room temperature, and the reaction system pH was adjusted to 1 with 2 mol/L HCl solution. The reaction mixture was extracted several times with ethyl acetate and water, and the organic phase was concentrated, dried over saturated brine and anhydrous sodium sulfate, and spin-dried. Silica gel powder (200-300 mesh) was added to the organic phase to mix. The column was packed with pure ethyl acetate, and sample was dry-loaded. The column chromatography was performed with the eluent (ethyl acetate:methanol was 20:1 v/v) to afford the product as a yellow viscous liquid (5.502 g, yield 27.5%).

a: $^1$H NMR (500 MHz, Chloroform-d) δ 6.46-6.15 (m, 3H), 4.15-4.10 (d, J=14.4 Hz, 1H), 4.01-3.96 (d, J=14.4 Hz, 1H), 1.19 (d, J=14.5 Hz, 9H); $^{13}$C NMR (126 MHz, Chloroform-d) δ 136.99, 125.79, 57.71, 31.53, 24.35; $^{31}$P NMR (162 MHz, Chloroform-d) δ 45.59; ESI-MS: m/z 163.00 [M+H]+.

2. Preparation of 3-(tert-butyl)-2-hydro-1,3-oxo-phosphoryl-3-oxy(b)

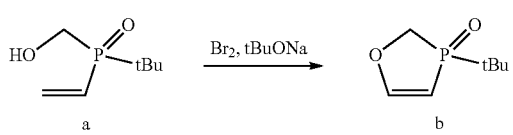

Under the protection of nitrogen, 10 g (25 mmol, 1 equivalent) of tert-butyl (hydroxymethyl) (vinyl) phosphine oxide was added into the dried Schlenk line, and 8 g (2.7 mL) of liquid bromine (50 mmol, 2 equivalents) and 50 mL of carbon tetrachloride were added. At an external temperature of 0° C., the mixture was magnetic stirred for about 0.5 h, then warmed to room temperature to react for 3 h. TLC (eluent: ethyl acetate:methanol=20:1 v/v, potassium permanganate as color developer) was used to detect the reaction. Post-treatment was performed after the reaction was completed. After the reaction was completed, the stirring bar was taken out and saturated sodium sulfite solution was gradually added dropwise until the orange-red color disappeared. Then the liquid was separated, the organic phase was taken and dried over anhydrous sodium sulfate, spin-dried to use in the next step.

4.8 g of sodium tert-butoxide (50 mmol, 2 equivalents) was added and reacted with 50 mL of tetrahydrofuran for 40 min TLC (eluent: ethyl acetate:methanol=20:1 v/v, potassium permanganate as color developer) was used to detect the reaction. Post-treatment was performed after the reaction was completed. After the reaction was completed, the stirring bar was taken out. Appropriate amount of silica gel powder was added and sample was dry-loaded. The column was packed with ethyl acetate. The column chromatography was performed by using eluent (ethyl acetate:methanol=80:1 v/v). The product was collected, concentrated and spin-dried to afford yellow oily liquid product (7.5 g, yield of 75%).

b: $^1$H NMR (500 MHz, Chloroform-d) δ 7.24-7.19 (dd, J=25.4, 4.7 Hz, 1H), 5.34-5.31 (dd, J=16.75, 4.7 Hz, 1H), 4.25 (dd, J=14.4, 3.9 Hz, 1H), 4.16 (dd, J=14.4, 10.2 Hz, 1H), 1.16 (d, fJ=16.0 Hz, 9H); $^{13}$C NMR (126 MHz, Chloroform-d) δ 163.89 (d, J=10.4 Hz), 91.75, 91.05, 64.39, 63.93, 32.25 (d, J=75.4 Hz), 24.37; $^{31}$P NMR (162 MHz, Chloroform-d) δ 72.56. ESI-MS: m/z 161.0 [M+H]+.

3. Preparation of 3-(tert-butyl)-2-hydro-1,3-oxa-phospholanyl-3-oxy(c)

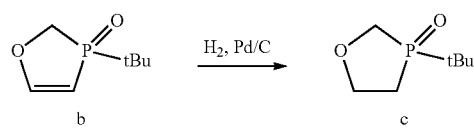 [SMILES: CC(C)(C)P1(=O)C=COC1 ; CC(C)(C)P1(=O)CCOC1]

1 g (6.2473 mmol, 1 equivalent) of 3-(tert-butyl)-2-hydro-1,3-oxaphospholanyl-3-oxy was put into the Schlenk line, 5 mL of ethyl acetate and 0.1 g of palladium carbon (10%) were added. After replaced with hydrogen under 1 atmosphere for three times, the reaction mixture was magnetic stirred at an external temperature of 40° C. for about 6 h, and cooled to room temperature after that. TLC (eluent: ethyl acetate:methanol=20:1 v/v, potassium permanganate as color developer) was used to detect the reaction. Post-treatment was performed after the reaction was completed. After the reaction was complete, the stirring bar was taken out. Appropriate amount of silica gel powder was added and sample was dry-loaded. The column was packed with ethyl acetate. The column chromatography was performed with the eluent (ethyl acetate:methanol=20:1 v/v), then the product was collected, concentrated and spin-dried to afford the product as a yellow oily liquid, 0.8904 g, yield 89%.

c: $^1$H NMR (500 MHz, Chloroform-d) δ 7.27 (s, OH), 4.19 (ddd, J=19.2, 9.5, 6.8 Hz, 1H), 4.12 (dd, J=13.2, 2.6 Hz, 1H), 4.04 (tt, J=10.0, 6.5 Hz, 1H), 3.59 (dd, J=13.2, 6.7 Hz, 1H), 1.23 (d, J=15.1 Hz, 9H); $^{13}$C NMR (126 MHz, Chloroform-d) δ 68.11, 64.19, 63.71, 31.79, 31.28, 24.27; $^{31}$P NMR (162 MHz, Chloroform-d) δ 48.63, 48.35, 48.01, 47.73. ESI-MS: m/z 163.05 [M+H]+.

4. Preparation of 3-(tert-butyl)-2-hydro-1,3-oxa-phospholanyl-3-sulfur (d)

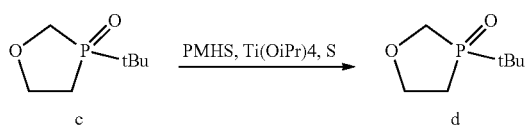 [SMILES: CC(C)(C)P1(=O)CCOC1 ; CC(C)(C)P1(=O)CCOC1]

Under the protection of nitrogen, 10 g (62.473 mmol, 1 equivalent) of 3-(tert-butyl)-2-hydro-1,3-oxaphospholanyl-3-oxy was put into the Schlenk line, 100 mL of tetrahydrofuran, 60.8 mL of polymethylhydrogensiloxane, and 25.2 mL of tetraisopropyl titanate (87.462 mmol, 1.4 equivalents) were added. The mixture was reacted at an external temperature of 70° C. for 4 h. TLC (eluent: ethyl acetate:methanol=10:1 v/v, potassium permanganate as color developer) was used to detect the reaction. Next step was performed after the reaction was completed. After the reaction was completed, the reaction system was cooled to 0° C., 3 g of sulfur powder (93.7 mmol, 1.5 equivalents) was slowly added dropwise, and the mixture was reacted at an external temperature of 0° C. for 1 h. TLC (eluent: ethyl acetate:methanol=2:1 v/v, potassium permanganate as color developer) was used to detect the reaction. Water was added to quench after the reaction was completed. The reaction solution was extracted with dichloromethane and water and separated, and the organic phase was dried.

Appropriate amount of silica gel powder was added and sample was dry-loaded. The column was packed with petroleum ether. The column chromatography was performed with the eluent (petroleum ether:ethyl acetate=20:1 v/v), then the product was collected, concentrated and spin-dried to afford the product as a white solid, 9.4 g, yield 86%.

d: $^1$H NMR (500 MHz, Chloroform-d) δ 4.47 (d, J=12.4 Hz, 1H), 4.37-4.25 (m, 1H), 4.01-3.94 (m, 1H), 3.63 (dd, J=12.4, 1.0 Hz, 1H), 2.43 (d, J=10.3 Hz, 1H), 2.05 (d, J=6.1 Hz, 1H), 1.28 (d, J=16.7 Hz, 9H); $^{13}$C NMR (126 MHz, Chloroform-d) δ 77.27, 77.02, 76.76, 70.80, 70.44, 69.02, 33.54, 33.19, 30.12, 29.70, 24.98, 24.96; $^{31}$P NMR (162 MHz, Chloroform-d) δ 76.17. ESI-MS: m/z 179.04 [M+H]+.

5. Preparation of R-3-(tert-butyl)-2-hydro-1,3-oxa-phospholanyl-3-sulfur (e-1)

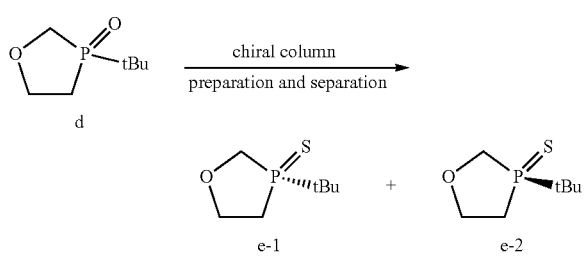

The compound was obtained by separating with chiral preparative column AD-H column. Specifically, the method comprises:

Preparing column model: CHIRALPAK AD-H, Particle Size=5 μm; Dimensions=4.6 mm*250 mm;

Mobile phase: isopropanol/n-hexane=5/95, Flow rate: 1 ml per minute; Detection wavelength: 210 nm. Retention time: $t_1$=7.1 min (S configuration), $t_2$=12.3 min (R configuration).

6. Preparation of R-3-(tert-butyl)-2-hydro-1,3-oxaphospholanyl-3-oxy (f-1)

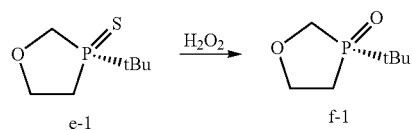

1 g (5.6 mmol, 1 equivalent) of R-3-(tert-butyl)-2-hydro-1,3-oxaphospholanyl-3-sulfur was put into the Schlenk line, 5 mL of methanol and 0.3 mL of hydrogen peroxide (30%) were added. The mixture was magnetic stirred at an external temperature of 30° C. for about 6 h. TLC (eluent: ethyl acetate:methanol=20:1 v/v, potassium permanganate as color developer) was used to detect the reaction. Post-treatment was performed after the reaction was completed. After the reaction was completed, the stirring bar was taken out. Appropriate amount of silica gel powder was added and the sample was dry-loaded. The column was packed with ethyl acetate. The column chromatography was performed with the eluent (petroleum ether:ethyl acetate=20:1 v/v). Then the product was collected, concentrated and spin-dried to afford the product as a yellow oily liquid, 0.86 g, yield 95%.

f-1: $^1$H NMR (500 MHz, Chloroform-d) δ 4.24-4.10 (m, 2H), 4.12 (dd, J=13.2, 2.6 Hz, 1H), 4.08-4.01 (m, 1H), 3.59-3.57 (dd, J=13.2, 6.7 Hz, 1H), 2.10-1.86 (m, 2H), 1.24-1.21 (d, J=15.1 Hz, 9H); $^{13}$C NMR (126 MHz, Chloroform-d) δ 68.11, 64.19, 63.71, 31.79, 31.28, 24.27; $^{31}$P NMR (162 MHz, Chloroform-d) δ 48.63, 48.35, 48.01, 47.73. ESI-MS: m/z 163.05 [M+H]$^+$.

7. Preparation of S-3-(tert-butyl)-2-hydro-1,3-oxaphospholanyl-3-borane (g)

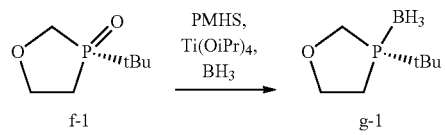

Under the protection of nitrogen, 5 g (30.8 mmol, 1 equivalent) of S-3-(tert-butyl)-2-hydro-1,3-oxaphospholanyl-3-oxy was added, and 50 mL of THF, 10 mL of polymethylhydrogensiloxane, and 11.6 mL of tetraisopropyl titanate (40 mmol, 1.3 equivalents) were added. The mixture was reacted at an external temperature of 70° C. for 4 h. TLC (eluent: ethyl acetate:methanol=10:1 v/v, potassium permanganate as color developer) was used to detect the reaction.

Next step was performed after the reaction was completed. After the reaction was completed, the reaction system was cooled to 0° C., and 36.9 mL of 1M borane tetrahydrofuran solution (36.9 mmol, 1.2 equivalents) was slowly added dropwise. The mixture was reacted at an external temperature of 0° C. for 1 h. TLC (eluent: petroleum ether:ethyl acetate=6:1 v/v, potassium permanganate as color developer) was used to detect the reaction. Saturated sodium hydroxide aqueous solution was immediately added to quench the reaction after the reaction was completed. The reaction solution was extracted with dichloromethane, separated, and the organic phase was dried. Appropriate amount of silica gel powder was added to the organic phase and sample was dry-loaded. The column was packed with petroleum ether. The column chromatography was performed with the eluent (petroleum ether:ethyl acetate=50:1 v/v), then the product was collected, concentrated and spin-dried to afford product as a white solid, 4.5 g, yield 90%.

g-1: $^1$H NMR (500 MHz, Chloroform-d) δ 4.43 (dd, J=12.3, 3.2 Hz, 1H), 4.27-4.19 (m, 1H), 3.73-3.66 (m, 2H), 2.10-2.01 (m, 2H), 1.21-1.18 (d, J=15), 0.9-0.21 (m, 3H); $^{13}$C NMR (126 MHz, Chloroform-d) δ 69.32, 69.29, 65.55, 65.34, 27.39, 27.18, 25.55, 25.53, 22.65, 22.38; $^{31}$P NMR (162 MHz, Chloroform-d) δ 48.18 (dd, J=100.6, 45.4 Hz). ESI-MS: m/z 163.1 [M+H]$^+$.

8. Preparation of (2R,2'R,3 S,3'S)-3,3'-di-tert-butyl-2,2'-bis(1,3-oxaphospholanyl)-3,3'-diborane (h-1)

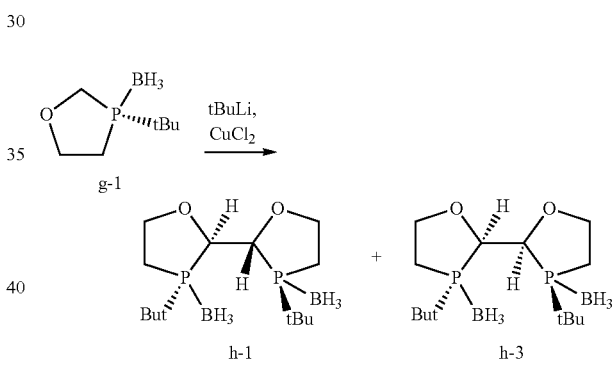

Under the protection of nitrogen, 2 g (12.3 mmol, 1 equivalent) of S-3-(tert-butyl)-2-hydro-1,3-oxaphospholanyl-3-borane was put into the Schlenk line, 10 mL of THF and 1.4 mL of TMEDA (18.5 mmol, 1.5 equivalents) were added. At an external temperature of −78° C., 10.9 mL of 1.7M tert-butyllithium (18.5 mmol, 1.5 equivalents) was added dropwise to the mixture at a rate of 2 drops/s and the resulting mixture was magnetic stirred for about 15 min. After that, 4.1 g of copper chloride (30.8 mmol, 2.5 equivalents) was added while the system was maintained at the external temperature of −78° C. The reaction mixture was warmed to room temperature to react for 45 min after addition. TLC (eluent: petroleum ether:ethyl acetate=6:1 v/v, potassium permanganate as color developer) was used to detect the reaction. Post-treatment was performed after the reaction was completed. After the reaction was completed, the reaction solution was extracted with ethyl acetate and 10% sodium hydroxide aqueous solution, separated, and the organic phase was dried. Appropriate amount of silica gel powder was added to the organic phase, and sample was dry-loaded.

The column was packed with petroleum ether. The column chromatography was performed with the eluent (petroleum ether:ethyl acetate=100:1 v/v), then the product was collected, concentrated and spin-dried to afford product as a white solid, 0.6 g, yield 30.6%.

h-1: $^1$H NMR (500 MHz, Chloroform-d) δ 4.39-4.37 (dd, 2H), 4.27-4.24 (m, 2H), 3.74 (m, 2H), 2.21-2.20 (m, 2H), 2.08-2.07 (m, 2H), 1.25 (d, J=13.9 Hz, 18H), 0.81-0.25 (m, 6H); $^{13}$C NMR (101 MHz, Chloroform-d) δ 73.67, 70.12, 28.34, 28.08, 25.71, 22.58, 22.26.; $^{31}$P NMR (162 MHz, Chloroform-d) δ 59.04. ESI-MS: m/z 321.21 [M+H]$^+$.

Single crystal X-ray diffraction: space group: P 21 21 2, unit cell parameters: a=10.2841(4) Å, b=11.1975(5) Å, c=8.5616(3) Å, α=90°, β=90°, γ=90°, unit cell volume: 985.92(7) Å$^3$.

The product h-3 was (2R,2'S, 3S, 3'S)-3,3'-di-tert-butyl-2,2'-bis(1,3-oxaphospholanyl)-3,3'-diborane: $^1$H NMR (500 MHz, Chloroform-d) δ 4.39-4.37 (dd, 1H), 4.34-4.31 (m, 1H), 4.23-4.17 (m, 2H), 4.02-3.95 (m, 1H), 3.74-3.68 (m, 1H), 2.24-2.06 (m, 4H), 1.29-1.23 (dd, 18H), 0.90-0.21 (m, 6H); $^{31}$P NMR (162 MHz, Chloroform-d) δ 60.78, 50.14. ESI-MS: m/z 321.21 [M+H]+.

Its single crystal X-ray diffraction: space group: P 21, unit cell parameters: a=7.4199(7) Å, b=24.550(3) Å, c=11.3537 (12) Å, α=90°, β=107.131(3)°, γ=90°, unit cell volume: 1976.4(4) Å$^3$.

9. Preparation of (2R,2'R,3S,3'S)-3,3'-di-tert-butyl-2,2'-bis(1,3-oxaphospholanyl) (1)

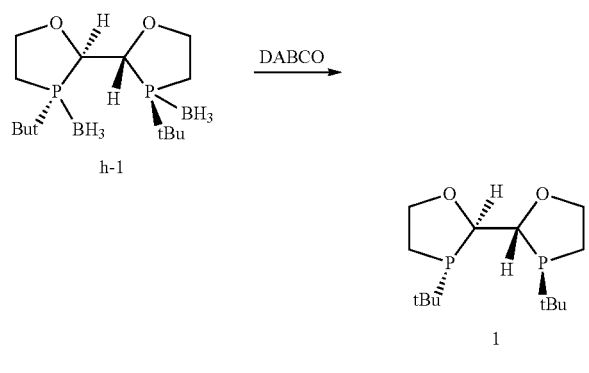

Under the protection of nitrogen, 100 mg (0.31 mmol, 1 equivalent) of (2R,2'R, 3S, 3'S)-3,3'-di-tert-butyl-2,2'-bis(1, 3-oxaphospholanyl)-3,3'-diborane was placed in Schlenk line. 6 mL of toluene and 105 mg of 1,4-diazabicyclo[2.2.2] octane (0.94 mmol, 3 equivalent) were added. The mixture was magnetic stirred for about 2 h at an external temperature of 60° C. Most of the toluene solvent was removed by the vacuum pump under reduced pressure. Degassed water (5 mL) was carefully added to the residue. At room temperature, degassed ether (5 mL) was added to the mixture, stirred at 60° C. for 0.5 hours, then separated to afford organic phase. The organic phase was dried over sodium sulfate, concentrated, and column chromatography purified on anhydrous oxygen-free neutral alumina (petroleum ether/ ether=3:1) to afford a colorless oily target ligand (2R,2'R, 3S, 3'S)-3,3'-di-tert-butyl-2,2'-bis(1,3-oxaphospholanyl) (68 mg, 75%).

1: $^1$H NMR (500 MHz, Chloroform-d) δ 4.79-4.77 (d, J=3.72, 2H), 4.20-4.17 (m, 4H), 2.16 (m, 4H), 1.24-1.19 (d, J=15); $^{31}$P NMR (162 MHz, Chloroform-d) δ 2.51. ESI-MS: m/z 291.21 [M+H]$^+$.

10. Preparation of Metal Complex {(norbornadiene) [(2R,2'R,3S,3'S)-3,3'-di-tert-butyl-2,2'-Bis(1,3-oxaphospholanyl)]}rhodium tetrafluoroborate, Namely Rh(nbd)(1)BF$_4$

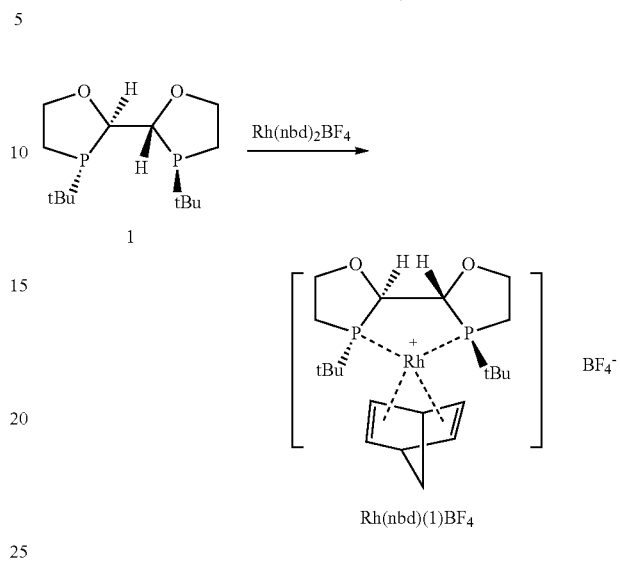

Under the protection of nitrogen, bis(norbornadiene)rhodium(I) tetrafluoroborate (18.7 mg, 0.05 mmol, 1 equivalent) was dissolved in tetrahydrofuran (0.5 mL). The tetrahydrofuran (0.5 mL) solution of ligand (2R,2'R, 3S, 3'S)-3, 3'-di-tert-butyl-2,2'-bis(1,3-oxaphospholanyl) (1, 16 mg, 0.055 mmol, 1.1 equivalent) was added with stirring system at 0° C. After the reaction system was stirred at room temperature for 0.5 hours, the vacuum pump was used for concentrating under reduced pressure to remove most of solvent. Degassed ether (10 mL) was added and stirred for 10 minutes, the mixture was filtered under nitrogen protection to afford the target compound {(norbornadiene)[(2R, 2'R,3S,3'S)-3,3'-di-tert-butyl-2,2'-bis(1,3-oxaphospholany 1)]} rhodium tetrafluoroborate, namely Rh(nbd)(1)BF$_4$ (43.4 mg, 0.0425 mmol, 85%).

Rh(nbd)(1)BF$_4$: $^1$H NMR (400 MHz, Chloroform-d) δ 6.98 (br s, 2H), 5.26 (s, 2H), 4.58-4.50 (m, 2H), 4.40-4.38 (d, J=10 Hz, 2H), 2.35 (br s, 2H), 2.17 (br s, 2H), 1.23-1.21 (d, J=10 Hz, 18H); $^{31}$P NMR (162 MHz, CDCl$_3$) δ 92.3-91.3, (d, 2J RhP=160 Hz).

Example 2

Preparation of (2S,2S,3R,3'R)-3,3'-di-tert-butyl-2,2'-bis(1,3-oxaphospholanyl) (2) and its metal complex 1(norbornadiene)[(2S,2S,3R,3'R)-3,3'-di-tert-butyl-2, 2'-bis(1,3-oxaphospholanyl)])rhodium tetrafluoroborate, Namely Rh(nbd)(2)BF$_4$ (the Reaction Route was Shown Below)

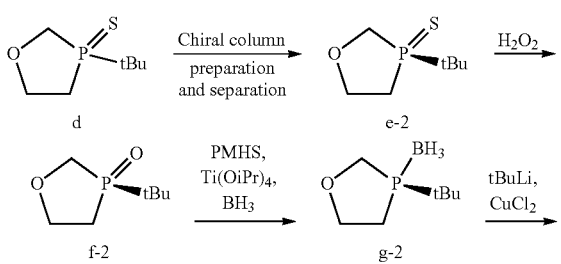

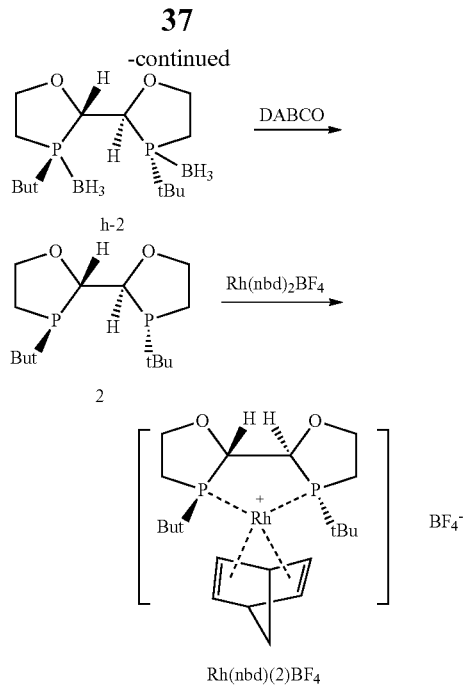

Rh(nbd)(2)BF₄

The compound e-2 preparation separated by the chiral column in step (5) of Example 1 was prepared according to the operation and conditions in Example 1. Preparation of S-3-(tert-butyl)-2-hydro-1,3-oxaphospholanyl-3-oxy 1 g (5.6 mmol, 1 equivalent) of S-3-(tert-butyl)-2-hydro-1,3-oxaphospholanyl-3-sulfur was put into Schlenk line. 5 mL of methanol and 0.3 mL of hydrogen peroxide (30%) were added. The mixture was magnetic stirred at an external temperature of 30° C. for about 6 h. TLC (eluent: ethyl acetate:methanol=20:1 v/v, potassium permanganate as color developer) was used to detect the reaction.

Post-treatment was performed after the reaction was completed. After the reaction was completed, the stirring bar was taken out. Appropriate amount of silica gel powder was added, and sample was dry-loaded. The column was packed with ethyl acetate. The column chromatography was performed with the eluent (ethyl acetate:methanol=20:1 v/v), then the product was collected, concentrated and spin-dried to afford product as a yellow oily liquid, 0.86 g, yield 95%.

f-2: $^1$H NMR (500 MHz, Chloroform-d) δ 4.24-4.10 (m, 2H), 4.12 (dd, J=13.2, 2.6 Hz, 1H), 4.08-4.01 (m, 1H), 3.59-3.57 (dd, J=13.2, 6.7 Hz, 1H), 2.10-1.86 (m, 2H), 1.24-1.21 (d, J=15.1 Hz, 9H); $^{13}$C NMR (126 MHz, Chloroform-d) δ 68.11, 64.19, 63.71, 31.79, 31.28, 24.27; $^{31}$P NMR (162 MHz, Chloroform-d) δ 48.63, 48.35, 48.01, 47.73. ESI-MS: m/z 163.05 [M+H]⁺.

Preparation of R-3-(Tert-Butyl)-2-Hydro-1,3-Oxaphospholanyl-3-Borane

Under the protection of nitrogen, 5 g (30.8 mmol, 1 equivalent) of S-3-(tert-butyl)-2-hydro-1,3-oxaphospholanyl-3-oxy was added. 50 mL of THF, 10 mL of polymethylhydrogensiloxane, and 11.6 mL of tetraisopropyl titanate (40 mmol, 1.3 equivalents) were added. The mixture was reacted at an external temperature of 70° C. for 4 h. TLC (eluent: ethyl acetate:methanol=10:1 v/v, potassium permanganate as color developer) was used to detect the reaction. Next step was performed after the reaction was completed. After the reaction was completed, the reaction system was cooled to 0° C., and 36.9 mL of 1M borane tetrahydrofuran solution (36.9 mmol, 1.2 equivalents) was slowly added dropwise. The mixture was reacted at an external temperature of 0° C. for 1 h. TLC (eluent: petroleum ether:ethyl acetate=6:1 v/v, potassium permanganate as color developer) was used to detect the reaction. When the reaction was completed, saturated sodium hydroxide aqueous solution was immediately added to quench the reaction. The reaction solution was extracted with dichloromethane, separated, and the organic phase was dried. Appropriate amount of silica gel powder was added to the organic phase, and sample was dry-loaded. The column was packed with petroleum ether. The column chromatography was performed with the eluent (petroleum ether:ethyl acetate=50:1 v/v), then the product was collected, concentrated and spin-dried to afford product as a white solid, 4.5 g, yield 90%.

g-2: $^1$H NMR (500 MHz, Chloroform-d) δ 4.43 (dd, J=12.3, 3.2 Hz, 1H), 4.27-4.19 (m, 1H), 3.73-3.66 (m, 2H), 2.10-2.01 (m, 2H), 1.21-1.18 (d, J=15), 0.9-0.21 (m, 3H); $^{13}$C NMR (126 MHz, Chloroform-d) δ 69.32, 69.29, 65.55, 65.34, 27.39, 27.18, 25.55, 25.53, 22.65, 22.38; $^{31}$P NMR (162 MHz, Chloroform-d) δ 48.18 (dd, J=100.6, 45.4 Hz). ESI-MS: m/z 163.1 [M+H]⁺.

Preparation of (2S,2'S,3R,3'R)-3,3'-di-tert-butyl-2, 2'-bis(1,3-oxaphospholanyl)-3,3'-diborane Under the protection of nitrogen, 2 g (12.3 mmol, 1 equivalent) of R-3-(tert-butyl)-2-hydro-1,3-oxaphospholanyl-3-borane was put into the Schlenk line. 10 mL of THF and 1.4 mL of TMEDA (18.5 mmol, 1.5 equivalents) were added. At an external temperature of −78° C., 10.9 mL of 1.7M tert-butyllithium (18.5 mmol, 1.5 equivalents) was added dropwise at a rate of 2 drops/s. The resulting mixture was magnetic stirred for about 15 min After that, 4.1 g of copper chloride (30.8 mmol, 2.5 equivalents) was added while the system was maintained at the external temperature of −78° C. Then the reaction mixture was warmed to room temperature to react for 45 min. TLC (eluent: petroleum ether:ethyl acetate=6:1 v/v, potassium permanganate as color developer) was used to detect the reaction. Post-treatment was performed after the reaction was completed. After the reaction was completed, the reaction solution was extracted with ethyl acetate and 10% sodium hydroxide aqueous solution, separated, and the organic phase was dried. Appropriate amount of silica gel powder was added to the organic phase, and sample was dry-loaded. The column was packed with petroleum ether. The column chromatography was performed with the eluent (petroleum ether:ethyl acetate=100:1 v/v), then the product was collected, concentrated and spin-dried. The product was obtained as a white solid, 0.6 g, yield 30.6%.

h-2: $^1$H NMR (500 MHz, Chloroform-d) δ 4.39-4.37 (dd, 2H), 4.27-4.24 (m, 2H), 3.74 (m, 2H), 2.21-2.20 (m, 2H), 2.08-2.07 (m, 2H), 1.25 (d, J=13.9 Hz, 18H), 0.81-0.25 (m, 6H); $^{13}$C NMR (101 MHz, Chloroform-d) δ 73.67, 70.12, 28.34, 28.08, 25.71, 22.58, 22.26.; $^{31}$P NMR (162 MHz, Chloroform-d) δ 59.04. ESI-MS: m/z 321.21 [M+H]⁺.

Preparation of (2S,2'S, 3R, 3'R)-3,3'-di-tert-butyl-2, 2'-bis(1,3-oxaphospholanyl)

Under the protection of nitrogen, 100 mg (0.31 mmol, 1 equivalent) of (2S,2'S,3R,3'R)-3,3'-di-tert-butyl-2,2'-bis(1, 3-oxaphospholanyl)-3,3'-diborane was placed in a Schlenk line, 6 mL of toluene, 105 mg of 1,4-diazabicyclo[2.2.2] octane (0.94 mmol, 3 equivalent) were added. The mixture was magnetic stirred for about 2 h at an external temperature of 60° C. Most of the toluene solvent was removed by the vacuum pump under reduced pressure. Degassed water (5 mL) was carefully added to the residue. Degassed ether (5 mL) was added to the mixed system at room temperature, and mixture was stirred at 60° C. for 0.5 hours, then separated to afford the organic phase. The organic phase was dried over with sodium sulfate, concentrated, and column chromatography purified on anhydrous oxygen-free neutral alumina (petroleum ether/ether=3:1) to obtain the colorless oily target ligand (2S,2'S, 3R, 3'R)-3,3'-di-tert-butyl-2,2'-bis (1,3-oxaphospholanyl) (68 mg, 75%).

2: $^1$H NMR (500 MHz, Chloroform-d) δ 4.79-4.77 (d, J=3.72, 2H), 4.20-4.17 (m, 4H), 2.16 (m, 4H), 1.24-1.19 (d, J=15); $^{31}$P NMR (162 MHz, Chloroform-d) δ 2.51. ESI-MS: m/z 291.21 [M+H]$^+$.

Preparation of Metal Complex {(norbornadiene)[(2S,2'S,3R,3'R)-3,3'-di-tert-butyl-2,2'-Bis(1,3-oxaphospholanyl)]}rhodium tetrafluoroborate, Namely Rh(nbd)(1)BF$_4$ Under the protection of nitrogen, bis(norbornadiene)rhodium(I) tetrafluoroborate (18.7 mg, 0.05 mmol, 1 equivalent) was dissolved in tetrahydrofuran (0.5 mL). The tetrahydrofuran (0.5 mL) solution of ligand (2S,2'S,3R,3'R)-3,3'-di-tert-butyl-2,2'-bis(1,3-oxaphospholanyl) (1, 16 mg, 0.055 mmol, 1.1 equivalent) was added with stirring at 0° C. The reaction system was stirred at room temperature for 0.5 hours, then concentrated under reduced pressure by vacuum pump to remove most of solvent. Degassed ether (10 mL) was added and stirred for 10 minutes, then the mixture was filtered under nitrogen protection to obtain the target compound {(norbornadiene)[ (2S,2'S,3R,3'R)-3,3'-di-tert-butyl-2,2'-bis(1,3-oxaphospholanyl)]} rhodium tetrafluoroborate, namely Rh(nbd)(2)BF$_4$ (43.4 mg, 0.0425 mmol, 85%).

Rh(nbd)(2)BF$_4$: $^1$H NMR (400 MHz, Chloroform-d) δ 6.98 (br s, 2H), 5.26 (s, 2H), 4.58-4.50 (m, 2H), 4.40-4.38 (d, J=10 Hz, 2H), 2.35 (br s, 2H), 2.17 (br s, 2H), 1.23-1.21 (d, J=10 Hz, 18H); $^{31}$P NMR (162 MHz, CDCl$_3$) δ 92.3-91.3, (d, 2J RhP=160 Hz).

Example 3

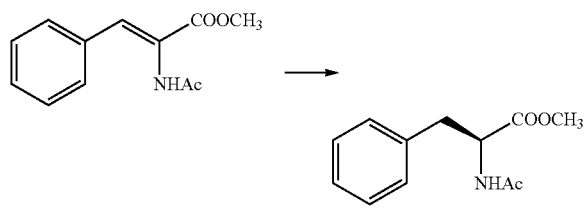

Methyl (Z)-2-acetamido-3-phenyl acrylate was used as the hydrogenation substrate and the chiral metal rhodium complex Rh(nbd)(1)BF$_4$ was used as the catalyst to prepare the optically active N-acetyl-L-phenylalanine methyl ester (S).

In a glove box, The reaction is as follows: under nitrogen atmosphere, methyl (Z)-2-acetamido-3-phenyl acrylate (22 mg, 0.1 mmol), Rh(nbd)(1)BF$_4$ (0.24 mg, 0.5 μmol), 0.5 mL of anhydrous dichloromethane were added to the hydrogenation flask, and transferred to the autoclave. After sealed, the autoclave was replaced with hydrogen for three times, and was charged with hydrogen to 750 psi. The system was reacted at 50° C. for 12 hours, and then cooled to room temperature. Hydrogen was discharged and the reactor was opened. The crude reaction product solution was filtered through microporous membrane to remove metal ions. After the solution was diluted by isopropanol, chiral AD-H column high performance liquid chromatography was used to measure the conversion rate and ee value of the product N-acetyl-L-phenylalanine methyl ester, which was 97%.

N-acetyl-L-phenylalanine methyl ester [(S)-3a]: white solid (yield>99%); 97% ee.

The ee value was determined by chiral high pressure liquid chromatography; high pressure liquid phase conditions: chiral AD-H column, 25° C., flow rate: 1 mL/min, n-hexane/isopropanol: 95/5, 210 nm, t$_1$=15.2 min (R), t$_2$=21.8 min (S).

$^1$H NMR (500 MHz, CDCl$_3$) δ 7.35-7.25 (m, 3H), 7.10-7.08 (d, J=10.45, 2H), 4.91-4.88 (dd, 2H), 3.74 (s, 1H), 3.13 (m, 2H), 1.99 (s, 1H).

Example 4

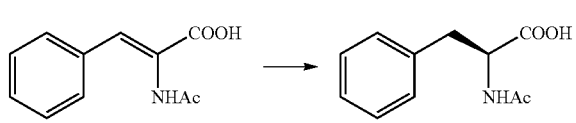 [SMILES: CC(=O)N/C(=C\c1ccccc1)C(=O)O ; CC(=O)N[C@@H](Cc1ccccc1)C(=O)O]

(Z)-2-acetamido-3-phenylacrylic acid was used as the hydrogenation substrate and the chiral metal rhodium complex Rh(nbd)(1)BF$_4$ was used as the catalyst to prepare the optically active N-acetyl-L-phenylalanine (S)-3b.

The reaction was as follows: under nitrogen atmosphere, in a glove box, (Z)-2-acetamido-3-phenylacrylic acid (20.5 mg, 0.1 mmol), Rh(nbd)(1)BF$_4$ (0.24 mg, 0.5 μmol), 0.5 mL of anhydrous dichloromethane were added to the hydrogenation flask, and transferred to the autoclave. After sealed, the autoclave was replaced with hydrogen for three times, and was charged with hydrogen to 750 psi. The system was reacted at 50° C. for 12 hours, then cooled to room temperature. Hydrogen was discharged and the reactor was opened. The crude reaction product solution was filtered through microporous membrane to remove metal ions. After the solution was diluted by isopropanol, chiral AD-H column high performance liquid chromatography was used to measure the conversion rate and ee value of the product N-acetyl-L-phenylalanine, which was 97%.

N-acetyl-L-phenylalanine [(S)-3b]: white solid (yield>99%); 98% ee.

The ee value was determined by chiral high pressure liquid chromatography; N-acetyl-L-phenylalanine was pre-transformed to N-acetyl-L-phenylalanine methyl ester in the presence of trimethylsilyl diazomethane. High pressure liquid phase conditions: chiral AD-H column, 25° C., flow rate: 1 mL/min, n-hexane/isopropanol: 95/5, 210 nm, t$_1$=15.2 min (S), t$_2$=21.8 min (R). $^1$H NMR (500 MHz, CD$_3$OD) δ 7.31-7.15 (m, 5H), 4.67-4.62 (dd, J=9.12, 4.98 Hz, 1H), 3.34 (d, J=0.63 Hz, 1H) 3.22-3.16 (dd, J=13.89, 5.04 Hz, 1H), 2.96-2.89 (dd, J=13.8, 9.2 Hz, 1H), 1.89 (s, 1H)

Example 5

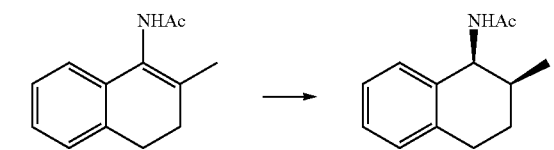

N-(2-methyl-3,4-dihydronaphthalene-1-yl)acetamide was used as the hydrogenation substrate and the chiral metal rhodium complex Rh(nbd)(1)BF₄ was used as the catalyst to prepare the optical active chiral amide (1S,2S)-3f.

The reaction is as follows: under nitrogen atmosphere, in a glove box, N-(2-methyl-3,4-dihydronaphthalene-1-yl)acetamide (20.1 mg, 0.1 mmol), Rh(nbd)(1)BF₄ (0.24 mg, 0.5 µmol), 0.5 mL of anhydrous dichloromethane were added to the hydrogenation flask, and transferred to the autoclave. After sealed, the autoclave was replaced with hydrogen for three times, and was charged with hydrogen to 750 psi. The system was reacted at 50° C. for 12 hours, then cooled to room temperature. Hydrogen was discharged and the reactor was opened. The crude reaction product solution was filtered through microporous membrane to remove metal ions. After the solution was diluted by isopropanol, chiral AD-H column high performance liquid chromatography was used to measure the conversion rate and ee value of the product N-((1S,2S)-2-methyl-1,2,3,4-tetrahydronaphthalene-1-yl) acetamide, which was 70%.

N-((1S,2S)-2-methyl-1,2,3,4-tetrahydronaphthalene-1-yl) acetamide white solid (yield>99%); 70% ee.

ee value was determined by chiral high pressure liquid chromatography; high pressure liquid phase conditions: chiral AD-H column, 25° C., flow rate: 1 mL/min, n-hexane/isopropanol: 95/5, 210 nm, t₁=8.7 min (S), t₂=11.8 min (R).
¹H NMR (500 MHz, CD₃OD) δ 7.24-7.00 (m, 4H), 5.60-5.42 (br s, 1H), 5.27-5.22 (dd, J=9.45, 4.2 Hz, 1H), 2.87-2.75 (m, 2H), 2.01 (s, 3H), 1.86-1.45 (m, 3H), 1.03-1.01 (d, J=6.8 Hz, 3H)
1H NMR (500 MHz, CDCl₃) δ 7.24-7.00 (m, 4H), 6.11 (d, 1H, J=9.3 Hz), 5.20-5.18 (dd, 1H, J=9.7, 4.7 Hz), 2.87-2.75 (m, 2H), 2.01-1.95 (m, 1H), 1.92 (s, 3H), 1.71-1.60 (m, 1H), 1.55-1.40 (m, 1H), 0.98 (d, 3H, J=6.9 Hz)

Example 6

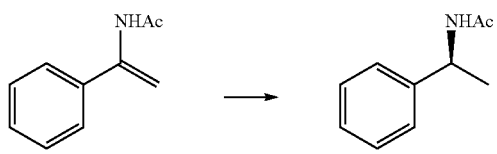

1-(acetylamino)-1-styrene was used as the hydrogenation substrate and the chiral metal rhodium complex Rh(nbd)(1)BF₄ was used as the catalyst to prepare the optically active chiral (S)—N-(1-phenylethyl)acetamide [(S)-3 h].

The reaction was as follows: under nitrogen atmosphere, in a glove box, 1-(acetylamino)-1-styrene (16 mg, 0.1 mmol), Rh(nbd)(1)BF₄ (0.24 mg, 0.5 µmol), and 0.5 mL of anhydrous dichloromethane were added to the hydrogenation flask and transferred to the autoclave. After sealed, the autoclave was replaced with hydrogen for three times, and was charged with hydrogen to 750 psi. The system was reacted at 50° C. for 12 hours, and then cooled to room temperature. Hydrogen was discharged and the reactor was opened. The crude reaction product solution was filtered through microporous membrane to remove metal ions. After the solution was diluted by isopropanol, chiral AD-H column high performance liquid chromatography was used to measure the conversion rate and ee value of the product (S)—N-(1-phenylethyl) acetamide [(S)-3 h], which was 99%.

(S)—N-(1-phenylethyl) acetamide: white solid (yield>99%); 99% ee.

The ee value was determined by chiral high pressure liquid chromatography; high pressure liquid phase conditions: chiral AD-H column, 25° C., flow rate: 1 mL/min, n-hexane/isopropanol: 95/5, 210 nm, t₁=10.1 min (S), t₂=12.8 min (R).

1H NMR (500 MHz, CDCl₃) δ 7.30-7.27 (m, 5H), 6.09 (br, 1H), 5.16-5.04 (m, 1H), 1.94 (s, 3H), 1.46 (d, J=6.8 Hz, 3H).

Example 7

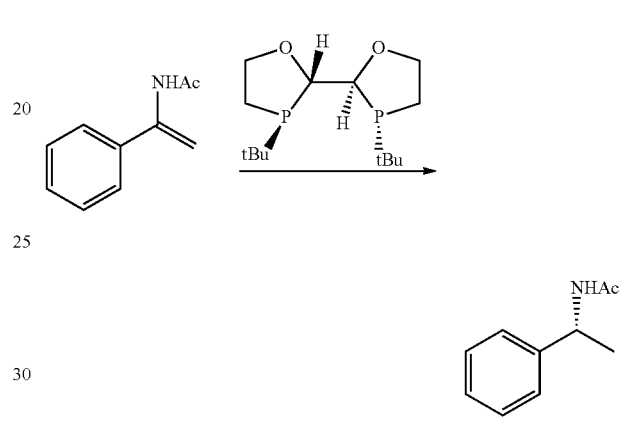

1-(Acetylamino)-1-styrene was used as the hydrogenation substrate, (2S,2S,3R,3'R)-3,3'-di-tert-butyl-2,2'-bis(1,3-oxaphospholanyl) was used as chiral phosphine ligand, Rh(nbd)₂BF₄ was used as metal catalyst to prepare the optically active chiral (R)—N-(1-phenylethyl)acetamide [(R)-3 h].

The reaction is as follows: under nitrogen atmosphere, in a glove box, 1-(acetylamino)-1-styrene (16 mg, 0.1 mmol), Rh(nbd)₂BF₄ (0.24 mg, 0.5 µmol), (2S,2S,3R,3'R)-3,3'-di-tert-butyl-2,2'-bis(1,3-oxaphospholanyl) (0.15 mg, 0.2 µmol), 0.5 mL of anhydrous dichloromethane were added to the hydrogenation flask and transferred to the autoclave. After sealed, the autoclave was, replaced with hydrogen for three times, and was charged with hydrogen to 750 psi. The system was reacted at 50° C. for 12 hours, and then cooled to room temperature. Hydrogen was discharged and the reactor was opened. The reaction crude product solution was filtered through microporous membrane to remove metal ions. After the solution was diluted by isopropanol, chiral AD-H column high performance liquid chromatography was used to measure the conversion rate and ee value of the product (S)—N-(1-phenylethyl) acetamide [(R)-3 h], which was 99%.

(S)—N-(1-phenylethyl) acetamide: white solid (yield>99%); 99% ee.

The ee value was determined by chiral high pressure liquid chromatography; high pressure liquid phase conditions: chiral AD-H column, 25° C., flow rate: 1 mL/min, n-hexane/isopropanol: 95/5, 210 nm, t₁=10.1 min (S), t₂=12.8 min (R). 1H NMR (500 MHz, CDCl₃) δ 7.36-7.20 (m, 5H), 6.02 (br s, 1H), 5.16-5.04 (m, 1H), 1.94 (s, 1H), 1.47-1.44 (d, J=11.4 Hz, 3H).

Example 8

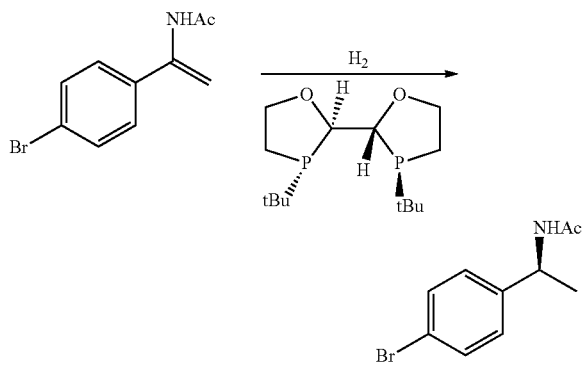

1-(4-Bromophenyl)-2-acetamidopropene was used as the hydrogenation substrate, (2R,2'R, 3S, 3'S)-3,3'-di-tert-butyl-2,2'-bis(1,3-oxaphospholanyl) was used as ligand, Rh(nbd)$_2$BF$_4$ was used as catalyst to prepare the optically active chiral (S)-1-(4-bromophenyl)-2-acetamido-propane.

The reaction is as follows: under nitrogen atmosphere, in a glove box, (E)-1-(4-bromophenyl)-2-acetamidopropene (4 g, 16.6 mmol), Rh(nbd)$_2$BF$_4$ (0.03 mg, 0.1 μmol), (2R,2'R, 3S, 3'S)-3,3'-di-tert-butyl-2,2'-bis(1,3-oxaphospholanyl) (0.03 mg, 0.1 μmol), 24 mL of anhydrous methanol were added to the hydrogenation flask and transferred to the autoclave. After sealed, the autoclave was replaced with hydrogen for three times, and was charged with hydrogen to 300 psi. The system was reacted at 25° C. for 12 hours, and then cooled to room temperature. Hydrogen was discharged and the reactor was opened. The crude reaction product solution was filtered through microporous membrane to remove metal ions. After the solution was diluted by isopropanol, chiral AD-H column high performance liquid chromatography was used to measure the conversion rate and ee value of the product N-acetyl-L-phenylalanine methyl ester, which was 97%.

(S)-1-(4-bromophenyl)-2-acetamido-propane: white solid (yield>99%); 98% ee.

The ee value was determined by chiral high pressure liquid chromatography; high pressure liquid phase conditions: chiral AD-H column, 25° C., flow rate: 1 mL/min, n-hexane/isopropanol: 95/5, 210 nm, t$_1$=13.4 min (S), t$_2$=17.9 min (R).

$^1$H NMR (400 MHz, CDCl$_3$) δ: 7.47 (d, J=8 Hz, 2H), 7.21 (d, J=8 Hz, 2H), 5.84 (s, br, 1H), 5.05-5.12 (m, 1H), 2.00 (s, 3H), 1.47 (d, J=4 Hz, 3H).

Example 9

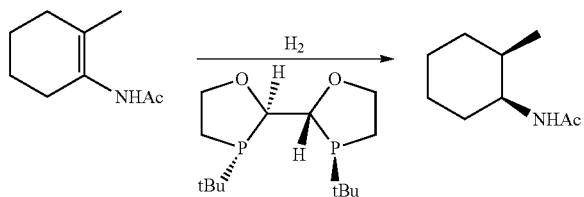

2-Methylcyclohexenyl 1-acetamide was used as hydrogenation substrate, (2R,2'R,3S,3'S)-3,3'-di-tert-butyl-2,2'-bis(1,3-oxaphospholanyl) was used as ligand, and Rh(nbd)$_2$BF$_4$ was used as catalyst were used to prepare the optically active chiral (1S,2R)-2-methylcyclohexyl-1-acetamide.

The reaction was as follows: under nitrogen atmosphere, in a glove box, 2-methylcyclohexenyl 1-acetamide (0.5 g, 3.2 mmol), Rh(nbd)$_2$BF$_4$ (1 mg, 2.4 μmol), (2R,2'R, 3S, 3'S)-3,3'-di-tert-butyl-2,2'-bis(1,3-oxaphospholanyl) (0.8 mg, 2.4 μmol), 5 mL of anhydrous methanol were added to the hydrogenation flask and transferred to the autoclave. After sealed, the autoclave was replaced with hydrogen three times, and was charged with hydrogen to 300 psi. The system was reacted at 25° C. for 12 hours, and then cooled to room temperature. Hydrogen was discharged and the reactor was opened. The crude reaction product solution was filtered through microporous membrane to remove metal ions. After the solution was diluted by isopropanol, chiral AD-H column high performance liquid chromatography was used to measure the conversion rate and ee value of the product (1S,2R)-2-methylcyclohexyl-1-acetamide, which was 68%.

(1S,2R)-2-methylcyclohexyl-1-acetamide: white solid (yield>99%); 68% ee.

The ee value was determined by chiral high pressure liquid chromatography; high pressure liquid phase conditions: chiral AD-H column, 25° C., flow rate: 1 mL/min, n-hexane/isopropanol: 95/5, 210 nm, t$_1$=11.2 min (1R,2S), t$_2$=12.1 min (1S,2R).

$^1$H NMR (400 MHz, CDCl$_3$) δ: 5.53 (s, 1H), 4.02-4.07 (m, 1H), 1.99 (s, 3H), 1.84 (m, 1H), 1.17-1.65 (m, 8H), 0.86 (d, J=7 Hz, 3H).

Example 10

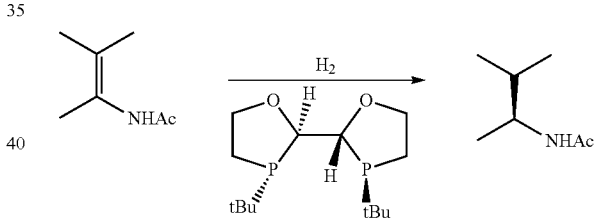

1,1-Dimethyl-2-acetamidopropene was used as hydrogenation substrate, (2R,2'R,3S,3'S)-3,3'-di-tert-butyl-2,2'-bis(1,3-oxaphospholanyl) was used as ligand, Rh(nbd)$_2$BF$_4$ was used as catalyst to prepare the optically active chiral (S)-1,1-dimethyl-2-acetamido-propane.

The reaction was as follows: under nitrogen atmosphere, in a glove box, 1,1-dimethyl-2-acetamidopropene (0.3 g, 2.4 mmol), Rh(nbd)$_2$BF$_4$ (0.7 mg, 2.4 μmol), (2R,2'R, 3S, 3'S)-3,3'-di-tert-butyl-2,2'-bis(1,3-oxaphospholanyl) (0.7 mg, 2.4 μmol), and 5 mL of anhydrous methanol were added to the hydrogenation flask and transferred to the autoclave. After sealed, the autoclave was replaced with hydrogen for three times, and was charged with hydrogen to 300 psi. The system was reacted at 25° C. for 12 hours, and then cooled to room temperature. Hydrogen was discharged and the reactor was opened. The crude reaction product solution was filtered through microporous membrane to remove metal ions. After the solution was diluted by ethyl acetate, chiral GC-MS column was used to measure the conversion rate and ee value of the product (S)-1-(4-bromophenyl)-2-acetamido-propane, which was 60%.

(S)-1-(4-bromophenyl)-2-acetamido-propane: white solid (yield>99%); 98% ee.

The ee value was determined by chiral GC-MS column; Chiral GC-MS conditions: FUSED SILICA Capillary Column, Beta DEX™ 225, 30 m*0.25 mm*0.25 uM film thickness. $t_1(S)$=11.18 min, $t_2(R)$=11.45 min. $^1$H NMR (500 MHz, CDCl$_3$) δ: 5.38 (s, 1H), 3.82-3.89 (m, 1H), 1.97 (s, 3H), 1.63-1.72 (m, 1H), 1.06 (d, J=6.7 Hz, 3H), 0.89 (d, J=5.4 Hz, 3H), 0.88 (d, J=6.2 Hz, 3H).

Example 11

1-(Acetylamino)-1-styrene was used as hydrogenation substrate, the chiral metal rhodium complex Rh(nbd)(1)BF$_4$ was used as catalyst to prepare the optically active chiral (S)—N-(1-phenylethyl)acetamide ((S)-3 h).

The reaction was as follows: under nitrogen atmosphere, in a glove box, 1-(acetylamino)-1-styrene (11 g, 68.2 mmol), Rh(nbd)(1)BF$_4$ (0.4 mg, 0.68 μmol), 110 mL of anhydrous dichloromethane were added to the hydrogenation flask and transferred to the autoclave. After sealed, the autoclave was replaced with hydrogen for three times, and was charged with hydrogen to 750 psi. The system was reacted at 50° C. for 12 hours, and then cooled to room temperature. Hydrogen was discharged and the reactor was opened. The crude reaction product solution was filtered through microporous membrane to remove metal ions. After the solution was diluted by isopropanol, chiral AD-H column high performance liquid chromatography was used to measure the conversion rate and ee value of the product (S)—N-(1-phenylethyl)acetamide [(S)-3 h], which was 99%.

(S)—N-(1-phenylethyl)acetamide: white solid (yield>99%); 99% ee.

The ee value was determined by chiral high pressure liquid chromatography; high pressure liquid phase conditions: chiral AD-H column, 25° C., flow rate: 1 mL/min, n-hexane/isopropanol: 95/5, 210 nm, $t_1$=10.1 min (S), $t_2$=12.8 min (R).

Comparative Example 1

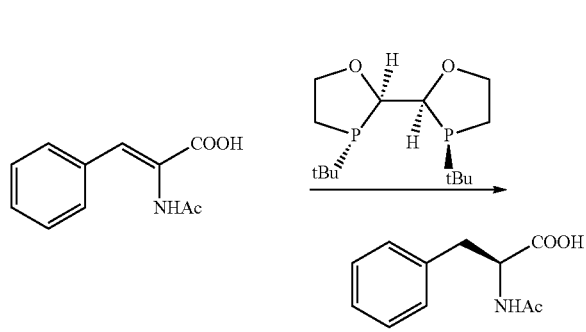

(Z)-2-acetamido-3-phenylacrylic acid was used as hydrogenation substrate, (2R,2S,3S,3'S)-3,3'-di-tert-butyl-2,2'-bis(1,3-oxaphospholanyl) (compound h-3) was used as chiral phosphine ligand, and Rh(nbd)$_2$BF$_4$ was used as metal catalyst to prepare the optically active chiral amide (S)-3b.

The reaction was as follows: under nitrogen atmosphere, in a glove box, (Z)-2-acetamido-3-phenylacrylic acid (20.5 mg, 0.1 mmol), Rh(nbd)$_2$BF$_4$ (0.19 mg, 0.5 μmol), (2S,2S,3R,3'R)-3,3'-di-tert-butyl-2,2'-bis(1,3-oxaphospholanyl) (0.15 mg, 0.5 μmol), and 0.5 mL of anhydrous dichloromethane were added to the hydrogenation flask and transferred to the autoclave. After sealed, the autoclave was replaced with hydrogen for three times, and was charged with hydrogen to 750 psi. The system was reacted at 50° C. for 12 hours, then cooled to room temperature. Hydrogen was discharged and the reactor was opened. The crude reaction product solution was filtered through microporous membrane to remove metal ions. After the solution was diluted by isopropanol, chiral AD-H column high performance liquid chromatography was used to measure the conversion rate and ee value of the product N-acetyl-L-phenylalanine, which was 58%.

N-acetyl-L-phenylalanine [(S)-3b]: white solid (yield>99%); 58% ee.

The ee value was determined by chiral high pressure liquid chromatography; N-acetyl-L-phenylalanine was pre-transformed to N-acetyl-L-phenylalanine methyl ester in the presence of trimethylsilyl diazomethane. High pressure liquid phase conditions: chiral AD-H column, 25° C., flow rate: 1 mL/min, n-hexane/isopropanol: 95/5, 210 nm, $t_1$=15.2 min (S), $t_2$=21.8 min (R). $^1$H NMR (500 MHz, CD$_3$OD) δ 7.31-7.15 (m, 5H), 4.67-4.62 (dd, J=9.12, 4.98 Hz, 1H), 3.34 (d, J=0.63 Hz, 1H) 3.22-3.16 (dd, J=13.89, 5.04 Hz, 1H), 2.96-2.89 (dd, J=13.8, 9.2 Hz, 1H), 1.89 (s, 1H)

Comparative Example 2

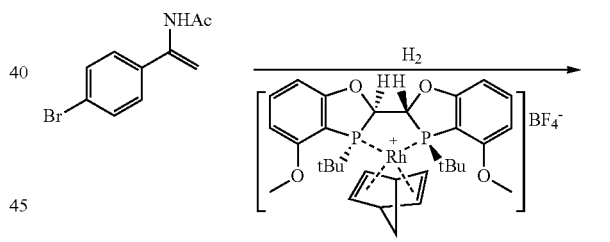

(E)-1-(4-bromophenyl)-2-acetamidopropene was used as the hydrogenation substrate, (2R,2'R,3R,3'R)-4,4'-bis(9-methoxy)-3,3'-di-tert-butyl-2,2',3,3'-tetrahydro-2,2'-dibenzo[d][1,3]oxaphospholanyl was used as ligand, Rh(nbd)$_2$BF$_4$ was used as catalyst to prepare the optically active chiral (S)-1-(4-bromophenyl)-2-acetamido-propane.

The reaction was as follows: under nitrogen atmosphere, in a glove box, 1-(4-bromophenyl)-2-acetamidopropene (4 g, 16.6 mmol), Rh(nbd)$_2$BF$_4$ (0.03 mg, 0.1 μmol), (2R,2'R, 3R,3'R)-4,4'-bis(9-methoxy)-3,3'-di-tert-butyl-2,2',3,3'-tetrahydro-2,2'-dibenzo[d][1,3]oxaphospholanyl (0.04 mg, 0.1

μmol), and 24 mL of anhydrous methanol were added to the hydrogenation flask and transferred to the autoclave. After sealed, the autoclave was replaced with hydrogen for three times, and was charged with hydrogen to 300 psi. The system was reacted at 25° C. for 12 hours, and then cooled to room temperature. Hydrogen was discharged and the reactor was opened. The crude reaction product solution was filtered through microporous membrane to remove metal ions. After the solution was diluted by isopropanol, chiral AD-H column high performance liquid chromatography was used to measure the conversion rate and ee value of the product (S)-1-(4-bromophenyl)-2-acetamido-propane, which was 91%.

(S)-1-(4-bromophenyl)-2-acetamido-propane: white solid (yield>99%); 91% ee.

The ee value was determined by chiral high pressure liquid chromatography; high pressure liquid phase conditions: chiral AD-H column, 25° C., flow rate: 1 mL/min, n-hexane/isopropanol: 95/5, 210 nm, $t_1$=13.4 min (S), $t_2$=17.9 min (R).

$^1$H NMR (400 MHz, CDCl$_3$) δ: 1.47 (d, J=4 Hz, 3H), 2.00 (s, 3H), 5.05-5.12 (m, 1H), 5.84 (s, br, 1H), 7.21 (d, J=8 Hz, 2H), 7.47 (d, J=8 Hz, 2H).

Comparative Example 3 replaced with hydrogen for three times, and hydrogen was charged to 300 psi. The system was reacted at 25° C. for 12 hours, and then cooled to room temperature. Hydrogen was discharged and the reactor was opened. The crude reaction product solution was filtered through a microporous membrane to remove metal ions. After the solution was diluted by isopropanol, chiral AD-H column high performance liquid chromatography was used to measure the conversion rate and ee value of the product (1R,2S)-2-methylcyclohexyl 1-acetamide, which was 20%.

(1S,2R)-2-methylcyclohexyl-1-acetamide: white solid (yield>99%); 20% ee.

The ee value was determined by chiral high pressure liquid chromatography; high pressure liquid phase conditions: chiral AD-H column, 25° C., flow rate: 0.7 mL/min, n-hexane/isopropanol: 95/5, 210 nm, $t_1$=11.2 min (1R,2S), $t_2$=12.1 min (1S,2R).

$^1$H NMR (400 MHz, CDCl$_3$) δ: 5.53 (s, 1H), 4.02-4.07 (m, 1H), 1.99 (s, 3H), 1.84 (m, 1H), 1.17-1.65 (m, 8H), 0.86 (d, J=7 Hz, 3H).

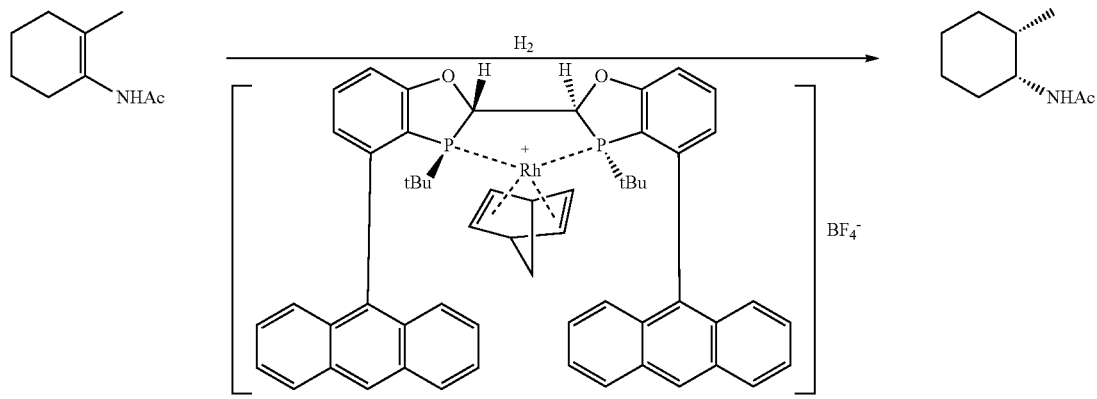

2-Methylcyclohexenyl 1-acetamide was used as the hydrogenation substrate, the metal complex {(norbornadiene)[(2S,2'S,3S,3'S)-4,4'-bis(9-anthryl)-3,3'-di-tert-butyl-2,2',3,3'-tetrahydro-2,2'-dibenzo[d][1,3]oxaphospholanyl}rhodium tetrafluoroborate was used as catalyst to prepare optically active chiral (1R,2S)-2-methylcyclohexyl 1-acetamide.

The reaction was as follows: under nitrogen atmosphere, in a glove box, 2-methylcyclohexenyl 1-acetamide (0.5 g, 3.2 mmol), the metal complex {(norbornadiene) [(2S,2'S,3S,3'S)-4,4'-bis(9-anthryl)-3,3'-di-tert-butyl-2,2',3,3'-tetrahydro-2,2'-dibenzo[d][1,3]oxaphospholanyl}rhodium tetrafluoroborate (2.2 mg, 2.4 μmol), 5 mL of anhydrous methanol were added to the hydrogenation flask and transferred to the autoclave. After sealed, the autoclave was Comparative Example 4

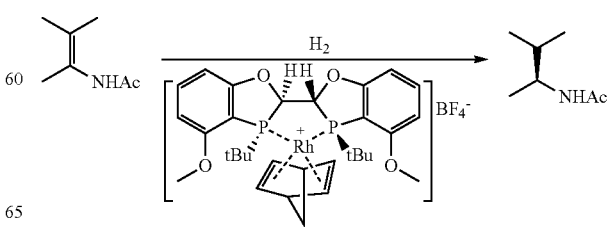

1,1-Dimethyl-2-acetamidopropene was used as the hydrogenation substrate, (2R,2'R,3R,3'R)-4,4'-bis(9-methoxy)-3,3'-di-tert-butyl-2,2',3,3'-tetrahydro-2,2'-dibenzo[d][1,3]oxaphospholanyl was used as ligand, Rh(nbd)$_2$BF$_4$ was used as catalyst to prepare the optically active chiral (S)-1,1-dimethyl-2-acetamido-propane.

The reaction is as follows: under nitrogen atmosphere, in a glove box, 1,1-dimethyl-2-acetamidopropene (0.1 g, 0.8 mmol), Rh(nbd)$_2$BF$_4$ (2 mg, 6 μmol), (2R,2'R,3R,3'R)-4,4'-bis(9-methoxy)-3,3'-di-tert-butyl-2,2',3,3'-tetrahydro-2,2'-dibenzo[d][1,3]oxaphospholanyl (4 mg, 9 μmol), and 5 mL of anhydrous methanol were added to the hydrogenation flask and transferred to the autoclave. After sealed, the autoclave was replaced with hydrogen for three times, and was charged with hydrogen to 300 psi. The system was reacted at 25° C. for 12 hours, and then cooled to room temperature. Hydrogen was discharged and the reactor was opened. The crude reaction product solution was filtered through a microporous membrane to remove metal ions. After the solution was diluted by isopropanol, chiral AD-H column high performance liquid chromatography was used to measure the conversion rate and ee value of the product (S)-1,1-dimethyl-2-acetamido-propane, which was 98%, yield 8%.

Comparative Example 5

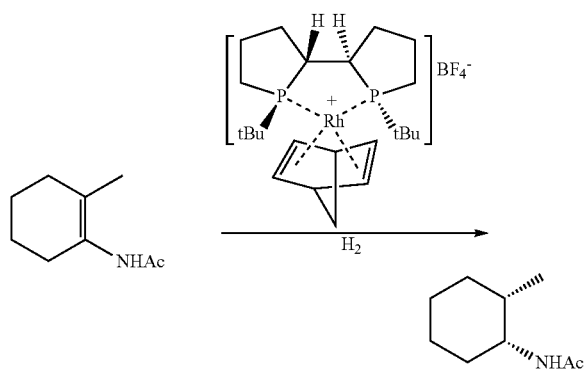

2-Methylcyclohexenyl 1-acetamide was used as the hydrogenation substrate, the metal complex {(norbornadiene) [(2 S,2' S,3R,3'R)-Tangphos]}rhodium tetrafluoroborate was used as the catalyst to prepare optically active chiral (1R,2S)-2-methylcyclohexyl 1-acetamide.

The reaction was as follows: under nitrogen atmosphere, in a glove box, 2-methylcyclohexenyl 1-acetamide (0.5 g, 3.2 mmol), the metal complex {(norbornadiene) [(2S,2'S,3R,3'R)-Tangphos]}rhodium tetrafluoroborate (1.4 mg, 2.4 μmol), 5 mL of anhydrous methanol were added to the hydrogenation flask and transferred to the autoclave. After sealed, the autoclave was replaced with hydrogen for three times, and was charged with hydrogen to 300 psi. The system was reacted at 25° C. for 12 hours, and then cooled to room temperature. Hydrogen was discharged and the reactor was opened. The crude reaction product solution was filtered through a microporous membrane to remove metal ions. After the solution was diluted by isopropanol, chiral AD-H column high performance liquid chromatography was used to measure the conversion rate and ee value of the product (1R,2S)-2-methylcyclohexyl 1-acetamide, which was 53%.

(1R,2S)-2-methylcyclohexyl-1-acetamide: white solid (yield>99%); 53% ee.

The ee value was determined by chiral high pressure liquid chromatography; high pressure liquid phase conditions: chiral AD-H column, 25° C., flow rate: 0.7 mL/min, n-hexane/isopropanol: 95/5, 210 nm, $t_1$=11.2 min (1R,2S), $t_2$=12.1 min (1S,2R).

The invention claimed is:

1. A metal complex according to Formula I:

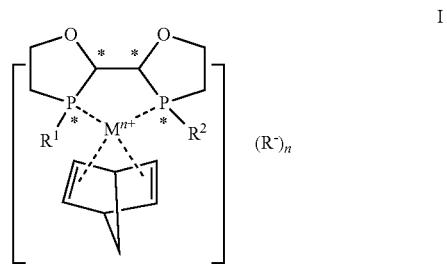

Wherein, $R^1$ and $R^2$ are each independently hydrogen, $C_1$-$C_{10}$ alkyl, $C_1$-$C_4$ alkoxy, $C_3$-$C_{30}$ cycloalkyl, halogen or $C_6$-$C_{30}$ aryl;

$M^{n+}$ is a transition metal ion; n is 1, 2 or 3, which corresponds to the ion valence of the transition metal M;

the carbons atoms marked with * are all S configuration chiral carbons or all R configuration chiral carbons;

the P marked with * are all S configuration chiral P or all R configuration chiral P;

$R^-$ is an anion.

2. The metal complex according to Formula I of claim 1, wherein when $R^1$ or $R^2$ are each independently $C_1$-$C_{10}$ alkyl, the $C_1$-$C_{10}$ alkyl is $C_{1-6}$ alkyl;

and/or, when $R^1$ or $R^2$ are each independently $C_1$-$C_4$ alkoxy, the $C_1$-$C_4$ alkoxy is methoxy, ethoxy, n-propoxy, iso-propoxy, n-butoxy, sec-butoxy, iso-butoxy or tert-butoxy;

and/or, when $R^1$ or $R^2$ are each independently $C_3$-$C_{30}$ cycloalkyl, the $C_3$-$C_{30}$ cycloalkyl is $C_3$-$C_8$ cycloalkyl;

and/or, when $R^1$ or $R^2$ are each independently $C_6$-$C_{30}$ aryl, the $C_6$-$C_{30}$ aryl is $C_6$-$C_{14}$ aryl;

and/or, when $R^1$ or $R^2$ are each independently halogen, the halogen is fluorine, chlorine, bromine or iodine;

and/or, the transition metal ion $M^{n+}$ is $Rh^+$, $Ru^{2+}$, $Ni^{2+}$, $Ir^{2+}$, $Pd^{2+}$, $Cu^{2+}$, $Pt^{2+}$, $Co^{2+}$ or $Au^{3+}$;

and/or, the anion $R^-$ is $BF_4^-$, $SbF_6^-$, $TfO^-$, $B(C_6H_5)_4^-$, $B[3,5\text{-}(CF_3)_2C_6H_3]_4^-$ or $PF_6^-$.

3. The metal complex according to Formula I of claim 2, wherein when $R^1$ or $R^2$ are each independently $C_1$-$C_6$ alkyl, the $C_{1-6}$ alkyl is methyl, ethyl, n-propyl, iso-propyl, n-butyl, sec-butyl, iso-butyl, tert-butyl, n-pentyl, iso-pentyl, neo-pentyl, or hexyl;

and/or, when $R^1$ or $R^2$ are each independently $C_3$-$C_8$ cycloalkyl, the $C_3$-$C_8$ cycloalkyl is cyclopropanyl, cyclobutanyl, cyclopentyl, cyclohexyl, cycloheptyl or cyclooctyl;

and/or, when $R^1$ or $R^2$ are each independently $C_6$-$C_{14}$ aryl, the $C_6$-$C_{14}$ aryl is phenyl or naphthyl;

and/or, the transition metal ion $M^{n+}$ is $Ru^{2+}$ or $Rh^+$;

and/or, the anion $R^-$ is $BF_4^-$ or $PF_6^-$;

and/or, $R^1$ is the same as $R^2$;

and/or, the metal complex according to Formula I is

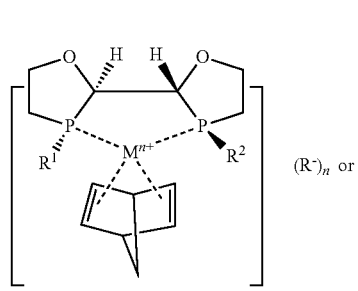

I-1

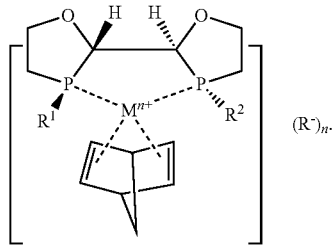

I-2

4. The metal complex according to Formula I of claim 1, wherein the metal complex according to Formula I is any one of the following compounds:

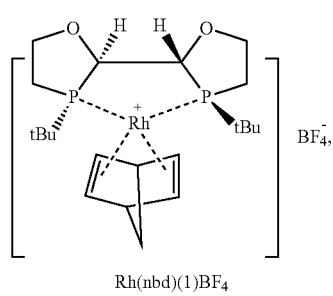

Rh(nbd)(1)BF$_4$

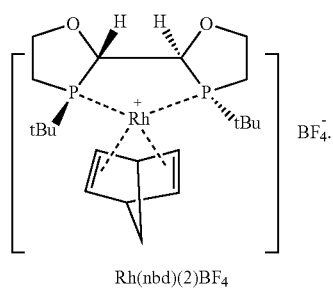

Rh(nbd)(2)BF$_4$

5. A method for preparing the metal complex according to Formula I of comprising: in an inert gas atmosphere, in an organic solvent, the transition metal precursor according to Formula III and the ligand compound according to Formula II are subjected to the complexation reaction shown below to afford the metal complex according to Formula I;

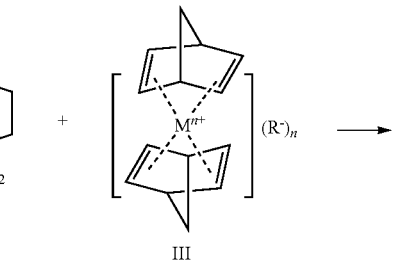

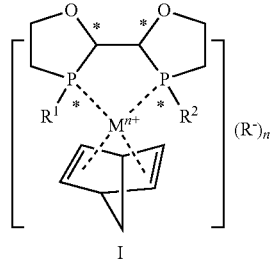

I wherein, the definitions of $R^1$, $R^2$, n and * are as described in claim 1.

6. A method for catalytic hydrogenation comprising in an organic solvent, in a hydrogen atmosphere and the presence of the metal complex according to Formula I, the compound A containing the structure of

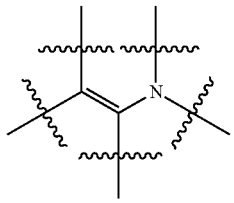 [SMILES: *C(*)=C(*)N(*)*]

is subjected to asymmetric catalytic hydrogenation reduction reaction to obtain the corresponding compound B;

wherein, when the metal complex according to Formula I

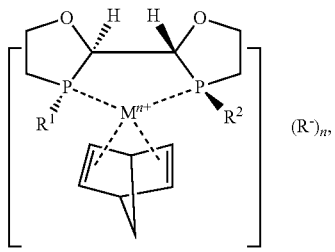

I-1 the predominant configuration of compound B contains the structure of

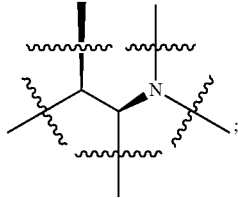

B-1 wherein, when the metal complex according to Formula I

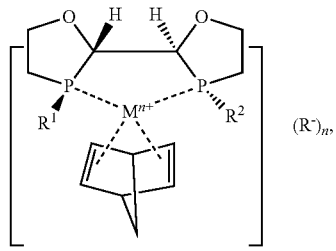

I-2 predominant configuration of compound B contains the structure of

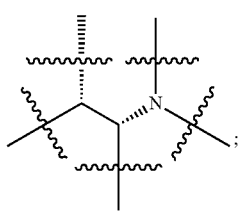

B-2 wherein, the definitions of $R^1$, $R^2$ and n are as described in claim 1.

7. The method of claim 6, wherein the compound A containing the structure of

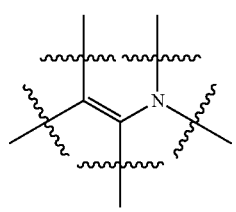

is of Formula A-1:

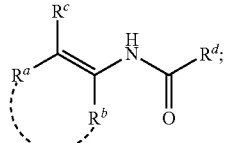

A-1 wherein, the dotted line represents no or ring formation;
$R^a$, $R^b$ and $R^c$ are each independently H, —COOH, —OH, —CN, optionally substituted alkyl-oxy, optionally substituted alkyl-oxy-carbonyl, optionally substituted alkyl-carbonyl-oxy, optionally substituted alkyl or cycloalkyl, optionally substituted heterocycloalkyl, optionally substituted aryl or optionally substituted heteroaryl;

or, $R^a$, $R^b$, together with the carbon atom to which they are connected, form optionally substituted cycloalkene or optionally substituted heterocycloalkene;

$R^d$ is independently optionally substituted alkyl or cycloalkyl, optionally substituted heterocycloalkyl, optionally substituted aryl or optionally substituted heteroaryl;

the "optionally substituted" is unsubstituted or substituted by the following groups: halogen, haloalkyl, —OH, —CN, alkyl-oxy, alkyl-S—, carboxyl, ester group, carbonyl, amido, optionally substituted aminosulfonyl or optionally substituted phenyl; the number of "substitution" is not limited; when being optionally substituted cycloalkenyl or optionally substituted heterocycloalkenyl, optionally substituted cycloalkyl, optionally substituted heterocycloalkyl, optionally substituted aryl or optionally substituted heteroaryl, the "substituted" refers to forming fused ring with the cycloalkene and heterocycloalkene, cycloalkyl, heterocycloalkyl, aryl or heteroaryl.

8. The method of claim 7, wherein, when $R^a$, $R^b$ or $R^c$ are optionally substituted alkyl, the optionally substituted alkyl is $C_1$-$C_{10}$ alkyl;

and/or, when $R^a$, $R^b$ or $R^c$ are optionally substituted alkyl-oxy-carbonyl, the optionally substituted alkyl-oxy-carbonyl is $C_1$-$C_6$ alkyl-oxy-carbonyl;

and/or, when $R^a$, $R^b$ or $R^c$ are optionally substituted aryl, the optionally substituted aryl is phenyl or halogen-substituted phenyl;

and/or, when "$R^a$, $R^b$, together with the carbon atom to which they are connected, form optionally substituted cycloalkene", the "optionally substituted cycloalkene" is benzocyclohexene or cyclohexene;

and/or, when $R^d$ is optionally substituted alkyl, the optionally substituted alkyl is $C_1$-$C_6$ alkyl.

9. The method of claim 8, wherein the compound A and the corresponding compound B-1 are selected from the following compounds:

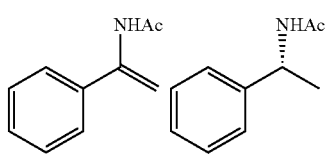

the compound A and the corresponding compound B-2 are selected from the following:
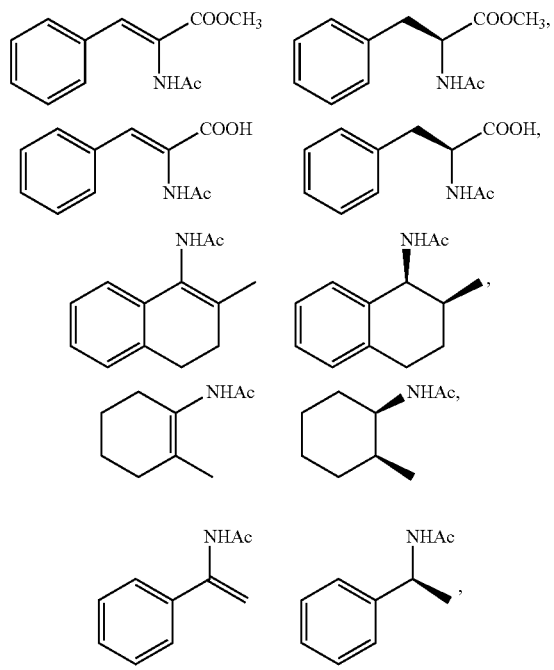
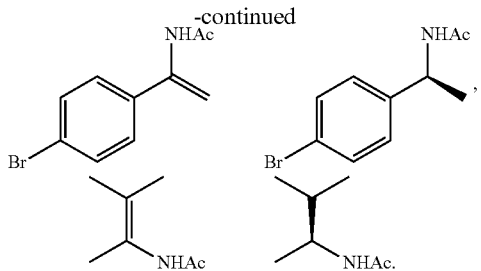
10. A compound II, which has any of the following structures:
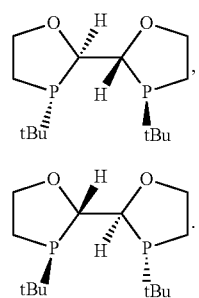
* * * * *